US008993651B2

(12) United States Patent
Chang et al.

(10) Patent No.: US 8,993,651 B2
(45) Date of Patent: Mar. 31, 2015

(54) POLYMERIZABLE CHAIN-EXTENDED POLYSILOXANES WITH PENDANT HYDROPHILIC GROUPS

(75) Inventors: Frank Chang, Suwanee, GA (US); Jinyu Huang, Suwanee, GA (US); Laura Ann Sanders, Decatur, GA (US)

(73) Assignee: Novartis AG, Basel (CH)

( * ) Notice: Subject to any disclaimer, the term of this patent is extended or adjusted under 35 U.S.C. 154(b) by 801 days.

(21) Appl. No.: 13/253,171

(22) Filed: Oct. 5, 2011

(65) Prior Publication Data

US 2012/0088843 A1 Apr. 12, 2012

Related U.S. Application Data

(60) Provisional application No. 61/390,448, filed on Oct. 6, 2010.

(51) Int. Cl.
| | |
|---|---|
| A01N 25/10 | (2006.01) |
| A61K 47/34 | (2006.01) |
| A01P 1/00 | (2006.01) |
| A61P 27/02 | (2006.01) |
| C08F 290/06 | (2006.01) |
| C08G 77/28 | (2006.01) |
| C08G 77/48 | (2006.01) |
| G02B 1/04 | (2006.01) |
| C08G 77/20 | (2006.01) |

(52) U.S. Cl.
CPC ............ *C08G 77/28* (2013.01); *C08F 290/068* (2013.01); *C08G 77/48* (2013.01); *G02B 1/043* (2013.01); *C08G 77/20* (2013.01)
USPC .......................................... 523/107; 525/479

(58) Field of Classification Search
CPC ................................ C08G 77/20; C08G 77/42
USPC .......................................... 503/107; 525/479
See application file for complete search history.

(56) References Cited

U.S. PATENT DOCUMENTS

| | | |
|---|---|---|
| 4,042,552 A | 8/1977 | Grueza |
| 4,045,547 A | 8/1977 | Le Boeuf et al. |
| 4,136,250 A | 1/1979 | Mueller et al. |
| 4,153,641 A | 5/1979 | Deichert et al. |
| 4,182,822 A | 1/1980 | Chang |
| 4,189,546 A | 2/1980 | Deichert et al. |
| 4,245,069 A | 1/1981 | Covington |
| 4,254,248 A | 3/1981 | Friends et al. |
| 4,259,467 A | 3/1981 | Keogh et al. |
| 4,260,725 A | 4/1981 | Keogh et al. |
| 4,261,875 A | 4/1981 | Le Boeuf |
| 4,276,402 A | 6/1981 | Chromecek et al. |
| 4,312,575 A | 1/1982 | Peyman et al. |
| 4,327,203 A | 4/1982 | Deichert et al. |
| 4,341,889 A | 7/1982 | Deichert et al. |
| 4,343,927 A | 8/1982 | Chang |
| 4,355,147 A | 10/1982 | Deichert et al. |
| 4,444,711 A | 4/1984 | Schad |
| 4,460,534 A | 7/1984 | Boehm et al. |
| 4,467,082 A | 8/1984 | Shirahata et al. |
| 4,486,577 A | 12/1984 | Mueller et al. |
| 4,543,398 A | 9/1985 | Bany et al. |
| 4,605,712 A | 8/1986 | Mueller et al. |
| 4,632,844 A | 12/1986 | Yanagihara et al. |
| 4,661,575 A | 4/1987 | Tom |
| 4,666,953 A | 5/1987 | Klemiarczyk et al. |
| 4,684,538 A | 8/1987 | Klemarczyk |
| 4,703,097 A | 10/1987 | Wingler et al. |
| 4,711,943 A | 12/1987 | Harvey, III |
| 4,833,218 A | 5/1989 | Lee |
| 4,837,289 A | 6/1989 | Mueller et al. |
| 4,954,586 A | 9/1990 | Toyoshima |
| 4,954,587 A | 9/1990 | Mueller |
| 4,983,702 A | 1/1991 | Mueller |
| 5,010,141 A | 4/1991 | Mueller |
| 5,034,461 A | 7/1991 | Lai |
| 5,039,761 A | 8/1991 | Ono |

(Continued)

FOREIGN PATENT DOCUMENTS

| | | |
|---|---|---|
| EP | 0216074 A2 | 4/1987 |
| EP | 0331633 A2 | 2/1989 |
| EP | 0379146 B1 | 7/1990 |
| EP | 0395583 A2 | 10/1990 |
| EP | 0425436 A2 | 5/1991 |
| EP | 0229033 B1 | 3/1993 |
| EP | 0455585 B1 | 3/1994 |
| EP | 0584826 B1 | 3/1994 |
| EP | 0677561 A1 | 10/1995 |
| EP | 0584764 B1 | 3/1997 |
| EP | 0862068 A2 | 9/1998 |
| EP | 0932635 B1 | 8/1999 |
| EP | 0958315 B1 | 11/1999 |
| EP | 0961941 B1 | 12/1999 |
| EP | 1197782 A1 | 4/2002 |
| EP | 1477511 A1 | 11/2004 |
| EP | 0862068 B1 | 6/2005 |

(Continued)

OTHER PUBLICATIONS

Authors: Y.F.Chang, T.M.Chen, Y.J.Li, M.Kitamura, and T.Nakaya Title of Article: Amphiphilic Poly(acrylamide)s Having Saturated and Unsaturated Dialkyl Chains and Phosphatidylcholine Groups in the Side Chains Published: Macromolecules 1996, vol. 29; No. 18; pp. 5810-5817.

(Continued)

*Primary Examiner* — Richard Schnizer
*Assistant Examiner* — Alma Pipic
(74) *Attorney, Agent, or Firm* — Jian Zhou

(57) ABSTRACT

The invention provide a class of chain-extended polysiloxane crosslinkers which comprises (1) at least two polysiloxane segments, wherein each pair of adjacent polysiloxane segments is linked by one divalent organic radical which includes at least one pendant hydrophilic group (hydroxyl and/or carboxyl groups) or at least one dangling hydrophilic polymer chain and a di-thioether linkage —S-DR-S— in which DR is a divalent organic radical; and (2) two terminal ethylenically unsaturated groups. The present invention is also related to a polymer comprising crosslinking units derived from chain-extended polysiloxane crosslinker of the invention and to ophthalmic lenses comprising such a polymer.

11 Claims, No Drawings

(56) References Cited

U.S. PATENT DOCUMENTS

| | | |
|---|---|---|
| 5,070,170 A | 12/1991 | Robertson |
| 5,070,215 A | 12/1991 | Bambury |
| 5,079,319 A | 1/1992 | Mueller |
| 5,164,462 A | 11/1992 | Yang |
| 5,194,556 A | 3/1993 | Mueller |
| 5,198,477 A | 3/1993 | von der Haegen |
| 5,219,965 A | 6/1993 | Valint, Jr. |
| 5,224,957 A | 7/1993 | Gasser |
| 5,227,432 A | 7/1993 | Jung |
| 5,244,981 A | 9/1993 | Seidner |
| 5,314,960 A | 5/1994 | Spinelli |
| 5,314,961 A | 5/1994 | Anton |
| 5,331,067 A | 7/1994 | Seidner |
| 5,346,946 A | 9/1994 | Yokoyama |
| 5,352,753 A | 10/1994 | Yang |
| 5,358,995 A | 10/1994 | Lai |
| 5,376,637 A | 12/1994 | Sawai |
| 5,387,632 A | 2/1995 | Lai |
| 5,416,132 A | 5/1995 | Yokoyama |
| 5,426,158 A | 6/1995 | Mueller |
| 5,449,729 A | 9/1995 | Lai |
| 5,451,617 A | 9/1995 | Lai |
| 5,466,768 A | 11/1995 | Yang |
| 5,480,927 A | 1/1996 | Janssen |
| 5,486,579 A | 1/1996 | Lai |
| 5,489,474 A | 2/1996 | Shinoda |
| 5,508,317 A | 4/1996 | Müller |
| 5,512,205 A | 4/1996 | Lai |
| 5,527,925 A | 6/1996 | Chabrecek |
| 5,559,163 A | 9/1996 | Dawson |
| 5,583,163 A | 12/1996 | Müller |
| 5,612,389 A | 3/1997 | Chabrecek |
| 5,612,391 A | 3/1997 | Chabrecek |
| 5,621,018 A | 4/1997 | Chabrecek |
| 5,637,726 A | 6/1997 | Collins |
| 5,663,288 A | 9/1997 | Shinoda |
| 5,665,840 A | 9/1997 | Pöhlmann |
| 5,681,871 A | 10/1997 | Molock |
| 5,712,356 A | 1/1998 | Bothe |
| 5,723,512 A | 3/1998 | Leppard |
| 5,729,322 A | 3/1998 | Collins |
| 5,760,100 A | 6/1998 | Nicolson |
| 5,767,169 A | 6/1998 | Leppard |
| 5,789,464 A | 8/1998 | Müller |
| 5,843,346 A | 12/1998 | Morrill |
| 5,849,810 A | 12/1998 | Müller |
| 5,849,811 A | 12/1998 | Nicolson |
| 5,849,841 A | 12/1998 | Mühlebach |
| 5,866,635 A | 2/1999 | Collins |
| 5,894,002 A | 4/1999 | Boneberger |
| 5,914,355 A | 6/1999 | Künzler |
| 5,959,117 A | 9/1999 | Ozark |
| 5,962,548 A | 10/1999 | Vanderlaan |
| 5,965,776 A | 10/1999 | Leppard |
| 5,981,615 A | 11/1999 | Meijs |
| 5,981,669 A | 11/1999 | Valint, Jr. |
| 5,981,675 A | 11/1999 | Valint, Jr. |
| 5,989,117 A | 11/1999 | Lin |
| 5,989,462 A | 11/1999 | Buazza |
| 5,998,498 A | 12/1999 | Vanderlaan |
| 6,015,842 A | 1/2000 | LeBoeuf |
| 6,015,874 A | 1/2000 | Hiratani |
| 6,020,445 A | 2/2000 | Vanderlaan |
| 6,020,528 A | 2/2000 | Leppard |
| 6,036,891 A | 3/2000 | Liao |
| 6,039,913 A | 3/2000 | Hirt |
| 6,096,846 A | 8/2000 | Oda |
| 6,136,880 A | 10/2000 | Snowwhite |
| 6,149,692 A | 11/2000 | Lally |
| 6,153,760 A | 11/2000 | Künzler |
| 6,162,844 A | 12/2000 | Lally |
| 6,165,408 A | 12/2000 | Steinmann |
| 6,204,300 B1 | 3/2001 | Kageoka |
| 6,204,306 B1 | 3/2001 | Chabrecek |
| 6,218,463 B1 | 4/2001 | Molock |
| 6,218,508 B1 | 4/2001 | Kragh |
| 6,221,303 B1 | 4/2001 | Steinmann |
| 6,252,032 B1 | 6/2001 | Van Antwerp |
| 6,284,813 B1 | 9/2001 | Leppard |
| 6,303,687 B1 | 10/2001 | Müller |
| 6,310,215 B1 | 10/2001 | Iwamoto |
| 6,312,706 B1 | 11/2001 | Lai |
| 6,329,485 B1 | 12/2001 | Vanderbilt |
| 6,342,570 B1 | 1/2002 | Bothe |
| 6,359,024 B2 | 3/2002 | Lai |
| 6,359,025 B1 | 3/2002 | Snowwhite |
| 6,361,925 B1 | 3/2002 | Leppard |
| 6,367,929 B1 | 4/2002 | Maiden |
| 6,376,568 B1 | 4/2002 | Baudin |
| 6,451,871 B1 | 9/2002 | Winterton |
| 6,465,538 B2 | 10/2002 | Lai |
| 6,472,489 B1 | 10/2002 | Stockinger |
| 6,479,587 B1 | 11/2002 | Stockinger |
| 6,492,478 B1 | 12/2002 | Steinmann |
| 6,596,294 B2 | 7/2003 | Lai |
| 6,627,124 B1 | 9/2003 | Herbrechtsmeier |
| 6,638,991 B2 | 10/2003 | Baba |
| 6,657,029 B2 | 12/2003 | Vanderbilt |
| 6,657,030 B2 | 12/2003 | Vanderbilt |
| 6,657,032 B2 | 12/2003 | Vanderbilt |
| 6,673,886 B2 | 1/2004 | Vanderbilt |
| 6,693,141 B2 | 2/2004 | Baudin |
| 6,713,583 B2 | 3/2004 | Liao |
| 6,719,929 B2 | 4/2004 | Winterton |
| 6,762,264 B2 | 7/2004 | Künzler |
| 6,767,169 B2 | 7/2004 | Zhan |
| 6,776,934 B2 | 8/2004 | Lai |
| 6,793,973 B2 | 9/2004 | Winterton |
| 6,800,225 B1 | 10/2004 | Hagmann |
| 6,811,804 B2 | 11/2004 | Patel |
| 6,811,805 B2 | 11/2004 | Gilliard |
| 6,822,016 B2 | 11/2004 | McCabe |
| 6,849,671 B2 | 2/2005 | Steffen |
| 6,852,353 B2 | 2/2005 | Qiu |
| 6,852,793 B2 | 2/2005 | Salamone |
| 6,858,218 B2 | 2/2005 | Lai |
| 6,884,457 B2 | 4/2005 | Gilliard |
| 6,896,926 B2 | 5/2005 | Qiu |
| 6,926,965 B2 | 8/2005 | Qiu |
| 6,940,580 B2 | 9/2005 | Winterton |
| 6,943,203 B2 | 9/2005 | Vanderlaan |
| 6,995,192 B2 | 2/2006 | Phelan |
| 7,040,756 B2 | 5/2006 | Qiu |
| 7,052,131 B2 | 5/2006 | McCabe |
| 7,071,274 B2 | 7/2006 | Fujisawa |
| 7,078,074 B2 | 7/2006 | Matsuzawa |
| 7,091,283 B2 | 8/2006 | Müller |
| 7,112,641 B2 | 9/2006 | Fujisawa |
| 7,214,809 B2 | 5/2007 | Zanini |
| 7,238,750 B2 | 7/2007 | Müller |
| 7,247,692 B2 | 7/2007 | Laredo |
| 7,249,848 B2 | 7/2007 | Laredo |
| 7,256,246 B2 | 8/2007 | Kindt-Larsen |
| 7,279,507 B2 | 10/2007 | Hu |
| 7,384,590 B2 | 6/2008 | Kelly |
| 7,387,759 B2 | 6/2008 | Kelly |
| 7,396,890 B2 | 7/2008 | Zanini |
| 7,416,737 B2 | 8/2008 | Alvarez-Carrigan |
| 7,423,108 B2 | 9/2008 | Kunzler |
| 7,461,937 B2 | 12/2008 | Steffen |
| 7,468,397 B2 | 12/2008 | Schorzman |
| 7,521,488 B2 | 4/2009 | Steffen |
| 7,550,519 B2 | 6/2009 | Phelan |
| 7,649,058 B2 | 1/2010 | McCabe |
| 7,666,921 B2 | 2/2010 | McCabe |
| 7,691,916 B2 | 4/2010 | McCabe |
| 2001/0037001 A1 | 11/2001 | Muller |
| 2002/0042022 A1 | 4/2002 | Leppard |
| 2002/0107297 A1 | 8/2002 | Baudin |
| 2002/0107324 A1 | 8/2002 | Vanderlaan |
| 2002/0198280 A1 | 12/2002 | Baba |
| 2003/0044447 A1 | 3/2003 | Zanini |
| 2003/0125498 A1 | 7/2003 | McCabe |
| 2003/0162862 A1 | 8/2003 | McCabe |

(56) References Cited

U.S. PATENT DOCUMENTS

| | | |
|---|---|---|
| 2004/0082680 A1 | 4/2004 | Phelan |
| 2004/0115242 A1 | 6/2004 | Meyers |
| 2004/0150788 A1 | 8/2004 | Anderson |
| 2004/0151755 A1 | 8/2004 | Rathore |
| 2004/0186248 A1 | 9/2004 | Vanderlaan |
| 2004/0209973 A1 | 10/2004 | Steffen |
| 2004/0213827 A1 | 10/2004 | Enns |
| 2005/0055090 A1 | 3/2005 | Lai |
| 2005/0113549 A1 | 5/2005 | Devlin |
| 2005/0117112 A1 | 6/2005 | Nayiby |
| 2005/0154080 A1 | 7/2005 | McCabe |
| 2005/0159502 A1 | 7/2005 | Steffen |
| 2005/0179862 A1 | 8/2005 | Steffen |
| 2005/0237483 A1 | 10/2005 | Phelan |
| 2005/0260249 A1 | 11/2005 | Neely |
| 2006/0007391 A1 | 1/2006 | McCabe |
| 2006/0036052 A1 | 2/2006 | Kindt-Larsen |
| 2006/0069178 A1 | 3/2006 | Rastogi |
| 2006/0235162 A1 | 10/2006 | Muller |
| 2006/0252850 A1 | 11/2006 | Jani |
| 2007/0043140 A1 | 2/2007 | Lorenz |
| 2007/0092830 A1 | 4/2007 | Lai |
| 2007/0092831 A1 | 4/2007 | Lai |
| 2007/0138692 A1 | 6/2007 | Ford |
| 2007/0142551 A1 | 6/2007 | Kunzler |
| 2007/0142584 A1 | 6/2007 | Schorzman |
| 2007/0160643 A1 | 7/2007 | Schorzman |
| 2007/0160649 A1 | 7/2007 | Schorzman |
| 2007/0161810 A1 | 7/2007 | Schorzman |
| 2007/0229757 A1 | 10/2007 | McCabe |
| 2007/0242215 A1 | 10/2007 | Schorzman |
| 2008/0000201 A1 | 1/2008 | Schorzman |
| 2008/0004413 A1 | 1/2008 | Schorzman |
| 2008/0004414 A1 | 1/2008 | Schorzman |
| 2008/0015282 A1 | 1/2008 | McCabe |
| 2008/0015315 A1 | 1/2008 | Chang |
| 2008/0076897 A1 | 3/2008 | Kunzler |
| 2008/0143003 A1 | 6/2008 | Phelan |
| 2008/0143958 A1 | 6/2008 | Medina |
| 2008/0174035 A1 | 7/2008 | Winterton |
| 2008/0231798 A1 | 9/2008 | Zhou |
| 2008/0234457 A1 | 9/2008 | Zhou |
| 2008/0274207 A1 | 11/2008 | Nayiby |
| 2008/0299179 A1 | 12/2008 | Rathore |
| 2008/0316424 A1 | 12/2008 | McCabe |
| 2009/0005528 A1 | 1/2009 | Fujisawa |
| 2009/0059164 A1 | 3/2009 | Steffen |
| 2009/0091704 A1 | 4/2009 | Steffen |
| 2009/0230575 A1 | 9/2009 | Liu |
| 2009/0234089 A1 | 9/2009 | Ueyama |
| 2009/0252868 A1 | 10/2009 | Phelan |
| 2009/0276042 A1 | 11/2009 | Hughes |
| 2010/0084775 A1 | 4/2010 | McCabe |
| 2010/0133710 A1 | 6/2010 | McCabe |
| 2010/0152084 A1 | 6/2010 | Rathore |
| 2010/0168359 A1 | 7/2010 | Domschke |

FOREIGN PATENT DOCUMENTS

| | | |
|---|---|---|
| EP | 1754728 B1 | 2/2010 |
| GB | 2002788 A | 2/1979 |
| GB | 2292740 A | 3/1996 |
| GB | 2310855 A | 9/1997 |
| WO | 92/09421 A2 | 6/1992 |
| WO | 9218548 A1 | 10/1992 |
| WO | 93/09084 A1 | 5/1993 |
| WO | 93/23773 A1 | 11/1993 |
| WO | 9628762 | 9/1996 |
| WO | 9631791 A1 | 10/1996 |
| WO | 9700274 A1 | 1/1997 |
| WO | 9805690 | 2/1998 |
| WO | 9825982 A1 | 6/1998 |
| WO | 9847954 | 10/1998 |
| WO | 9933894 | 7/1999 |
| WO | 00/31150 A1 | 6/2000 |
| WO | 0031150 A1 | 6/2000 |
| WO | 0059970 | 10/2000 |
| WO | 0107523 A1 | 2/2001 |
| WO | 01/71392 A1 | 9/2001 |
| WO | 2006055409 A2 | 5/2006 |
| WO | 2007128051 A1 | 11/2007 |
| WO | 2007146137 A2 | 12/2007 |
| WO | 2007146299 A2 | 12/2007 |
| WO | 2007146312 A2 | 12/2007 |
| WO | 2008/008752 A2 | 1/2008 |
| WO | 2008116131 A2 | 9/2008 |

OTHER PUBLICATIONS

PCT International Search Report dated Feb. 14, 2012, International Application No. PCT/US2011/054865, International Filing Date Oct. 5, 2011.

PCT Written Opinion of the International Searching Authority dated Feb. 14, 2012, International Application No. PCT/US2011/054865, International Filing Date Oct. 5, 2011.

POLYMERIZABLE CHAIN-EXTENDED POLYSILOXANES WITH PENDANT HYDROPHILIC GROUPS

This application claims the benefit under 35 USC §119 (e) of U.S. provisional application No. 61/390,448 filed 6 Oct. 2010, incorporated by reference in its entirety.

The present invention is related to a class of polymerizable chain-extended polysiloxane with pendant hydrophilic groups and uses thereof. The present invention is also related to a polymer which is a polymerization product of a polymerizable chain-extended polysiloxane of the invention with one or more other polymerizable compounds and to silicone hydrogel contact lenses made from a lens formulation including a polymerizable chain-extended polysiloxane of the invention.

BACKGROUND

In recent years, soft silicone hydrogel contact lenses become more and more popular because of their high oxygen permeability and comfort. "Soft" contact lenses can conform closely to the shape of the eye, so oxygen cannot easily circumvent the lens. Soft contact lenses must allow oxygen from the surrounding air (i.e., oxygen) to reach the cornea because the cornea does not receive oxygen from the blood supply like other tissue. If sufficient oxygen does not reach the cornea, corneal swelling occurs. Extended periods of oxygen deprivation cause the undesirable growth of blood vessels in the cornea. By having high oxygen permeability, a silicone hydrogel contact lens allows sufficient oxygen permeate through the lens to the cornea and to have minimal adverse effects on corneal health.

One of lens forming materials widely used in making silicone hydrogel contact lenses is polymerizable polysiloxane. The main function of the polymerizable polysiloxane is to provide high oxygen permeability to resultant contact lenses. However, because of its hydrophobic nature, a polymerizable polysiloxane is generally not compatible with hydrophilic components in a lens formulation, including, e.g., hydroxyethylmethacrylate, hydroxyethylacrylate, N,N-dimethylacrylamide, N-vinylpyrrolidone, or an internal wetting agent. It would be difficult to obtain homogeneous lens formulations.

Therefore, there is a need for new actinically-polymerizable polysiloxanes which are relatively more compatible with the hydrophilic components of a lens formulation for making silicone hydrogel contact lenses.

SUMMARY OF THE INVENTION

The present invention, in one aspect, provides a linear actinically-polymerizable chain-extended polysiloxane crosslinker. The chain-extended polysiloxane crosslinker of the invention comprises: (1) at least two polysiloxane segments; (2) one divalent organic radical between each pair of polysiloxane segments, wherein each divalent organic radical includes at least two pendant hydrophilic groups and/or chains; and (3) two actinically-polymerizable terminal groups.

In another aspect, the invention provides a polymer comprising polymer units derived from at least one polymerizable chain-extended polysiloxane crosslinker of the invention.

In a further aspect, the invention provides silicone hydrogel contact lens, which comprises: a polymeric material that is obtained by polymerizing a lens-forming material including a polymerizable chain-extended polysiloxane crosslinker of the invention in a mold.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" or "hydrogel material" refers to a polymeric material which can absorb at least 10 percent by weight of water when it is fully hydrated.

A "silicone hydrogel" refers to a silicone-containing hydrogel obtained by copolymerization of a polymerizable composition comprising at least one silicone-containing vinylic monomer or crosslinker or at least one actinically-crosslinkable silicone-containing prepolymer.

"Hydrophilic," as used herein, describes a material or portion thereof that will more readily associate with water than with lipids.

A "vinylic monomer", as used herein, refers to a compound that has one sole ethylenically unsaturated group and can be polymerized actinically or thermally.

The term "olefinically unsaturated group" or "ethylenically unsaturated group" is employed herein in a broad sense and is intended to encompass any groups containing at least one >C=C< group. Exemplary ethylenically unsaturated groups include without limitation (meth)acryloyl

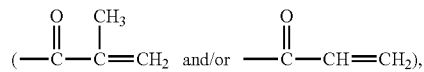

allyl, vinyl, styrenyl, or other C=C containing groups.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionizing radiation (e.g. gamma ray or X-ray irradiation), microwave irradiation, and the like. Thermal curing or actinic curing methods are well-known to a person skilled in the art.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which as a homopolymer typically yields a polymer that is water-soluble or can absorb at least 10 percent by weight water.

A "hydrophobic vinylic monomer", as used herein, refers to a vinylic monomer which as a homopolymer typically yields a polymer that is insoluble in water and can absorb less than 10 percent by weight water.

A "prepolymer" refers to a polymer that contains ethylenically unsaturated groups and can be polymerized actinically or thermally to form a polymer having a molecular weight larger than the starting prepolymer.

A "polymer" means a material formed by polymerizing/crosslinking one or more vinylic monomers, crosslinkers and/or prepolymers.

"Molecular weight" of a polymeric material (including monomeric or macromeric materials), as used herein, refers to the weight-average molecular weight unless otherwise specifically noted or unless testing conditions indicate otherwise.

A "crosslinker" refers to a compound having at least two ethylenically-unsaturated groups. A "crosslinking agent" refers to a compound which belongs to a subclass of crosslinkers and comprises at least two ethylenically unsaturated groups and has a molecular weight of 700 Daltons or less.

A "polysiloxane" refers to a compound containing one sole polysiloxane segment.

A "chain-extended polysiloxane" refers to a compound containing at least two polysiloxane segments separated by a linkage.

A "polysiloxane vinylic monomer" refers to a vinylic monomer containing one sole ethylenically unsaturated group and at least one sole polysiloxane segment.

A "chain-extended polysiloxane vinylic monomer" refers to a compound which comprises one sole ethylenically unsaturated group and at least two polysiloxane segments separated by a linkage.

The term "polysiloxane segment" refers to a divalent radical of formula (1)

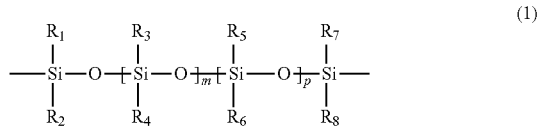

in which $R_1$, $R_2$, $R_3$, $R_4$, $R_5$, $R_6$, $R_7$, and $R_8$, independently of one another, are $C_1$-$C_{10}$ alkyl, di-$C_1$-$C_3$ alkylaminoalkyl, $C_1$-$C_{10}$ hydroxyalkyl, $C_1$-$C_{10}$ ether, $C_1$-$C_4$ alkyl- or $C_1$-$C_4$—alkoxy-substituted phenyl, $C_1$-$C_{10}$ fluoroalkyl, $C_1$-$C_{10}$ fluoroether, $C_6$-$C_{18}$ aryl radical, cyano($C_1$-$C_{12}$-alkyl), -alk-$(OCH_2CH_2)_n$—$OR_9$ in which alk is $C_1$-$C_6$-alkylene divalent radical, $R_9$ is hydrogen or $C_1$-$C_5$ alkyl and n is an integer from 1 to 20, m and p independently of each other are an integer of from 0 to 150 and (m+p) is from 1 to 150.

A "polysiloxane crosslinker" refers to a compound having at least two ethylenically unsaturated groups and one sole polysiloxane segment.

A "chain-extended polysiloxane crosslinker" refers to a linear polysiloxane compound which comprises at least two ethylenically unsaturated groups and at least two polysiloxane segments separated by a linkage.

The term "fluid" as used herein indicates that a material is capable of flowing like a liquid.

A free radical initiator can be either a photoinitiator or a thermal initiator. A "photoinitiator" refers to a chemical that initiates free radical crosslinking/polymerizing reaction by the use of light. Suitable photoinitiators include, without limitation, benzoin methyl ether, diethoxyacetophenone, a benzoylphosphine oxide, 1-hydroxycyclohexyl phenyl ketone, Darocure® types of photoinitiators, and Irgacure® types of photoinitiators, preferably Darocure® 1173, and Irgacure® 2959. Examples of benzoylphosphine oxide initiators include 2,4,6-trimethylbenzoyldiphenylophosphine oxide (TPO); bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a prepolymer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

A "thermal initiator" refers to a chemical that initiates radical crosslinking/polymerizing reaction by the use of heat energy. Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator is 2,2'-azobis(isobutyronitrile) (AIBN).

A "polymerizable UV-absorbing agent" refers to a compound comprising an ethylenically-unsaturated group and a UV-absorbing moiety which can absorb or screen out UV radiation in the range from 200 nm to 400 nm as understood by a person skilled in the art.

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary, as illustrated in U.S. Pat. Nos. 6,800,225, 6,627,124, 7,384,590 and 7,387,759 (all of which are incorporated by reference in their entireties).

"Dye" means a substance that is soluble in a lens-forming fluid material and that is used to impart color. Dyes are typically translucent and absorb but do not scatter light.

A "pigment" means a powdered substance (particles) that is suspended in a lens-forming composition in which it is insoluble.

A "hydrophilic surface" in reference to a silicone hydrogel material or a contact lens means that the silicone hydrogel material or the contact lens has a surface hydrophilicity characterized by having an averaged water contact angle of about 90 degrees or less, preferably about 80 degrees or less, more preferably about 70 degrees or less, even more preferably about 60 degrees or less.

An "average water contact angle" refers to a water contact angle (measured by Sessile Drop), which is obtained by averaging measurements of at least 3 individual contact lenses or samples of a silicone hydrogel material.

An "antimicrobial agent", as used herein, refers to a chemical that is capable of decreasing or eliminating or inhibiting the growth of microorganisms such as that term is known in the art. Preferred examples of antimicrobial agent include without limitation silver salts, silver complexes, silver nanoparticles, silver-containing zeolites, and the likes "Silver nanoparticles" refer to particles which are made essentially of silver metal and have a size of less than 1 micrometer.

The term "soluble" in reference to a polysiloxane or prepolymer of the invention means that the polysiloxane or prepolymer can be dissolved in a solvent to an extent sufficient to form a solution of the prepolymer having a concentration of at least about 1% by weight at room temperature (about 22° C. to about 28° C.).

The term "water solubility and/or dispersity" in reference to a prepolymer of the invention means the concentration (weight percentage) of the prepolymer dissolved and/or dispersed in water at room temperature (about 22° C. to about 28° C.) to form a transparent aqueous solution or a slightly hazy aqueous solution having a light transmissibility of 85% or greater in the range between 400 to 700 nm.

In accordance with the invention, the term "oxygen permeability" in reference to a contact lens means an estimated intrinsic oxygen permeability $Dk_c$ which is corrected for the surface resistance to oxygen flux caused by the boundary layer effect as measured according to the procedures described in Example 1. The intrinsic "oxygen permeability", Dk, of a material is the rate at which oxygen will pass through a material. Oxygen permeability is conventionally expressed in units of barrers, where "barrer" is defined as $[(cm^3\ oxygen)(mm)/(cm^2)(sec)(mm\ Hg)] \times 10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as $[(cm^3\ oxygen)/(cm^2)(sec)(mm\ Hg)] \times 10^{-9}$.

The "ion permeability" through a lens correlates with the Ionoflux Diffusion Coefficient. The Ionoflux Diffusion Coefficient, D (in units of $[mm^2/min]$), is determined by applying Fick's law as follows:

$$D = -n'/(A \times dc/dx)$$

where n'=rate of ion transport [mol/min]; A=area of lens exposed $[mm^2]$; dc=concentration difference [mol/L]; dx=thickness of lens [mm].

In general, the invention is directed to a class of actinically-crosslinkable chain-extended polysiloxane crosslinkers with two or more polysiloxane segments each pair of which is covalently linked together by a linker having two or more pendant hydrophilic groups, such as, hydroxyl groups and/or carboxyl groups.

There are several potential unique features associated with use of chain-extended polysiloxane crosslinkers of the invention in making silicone hydrogel contact lens. First, a chain-extended polysiloxane crosslinker of the invention in a silicone hydrogel contact lens formulation can be used to significantly improve the compatibility of polymerizable polysiloxane with other hydrophilic ingredients, such as, for example, a hydrophilic vinylic monomer and optionally a leachable polymeric wetting agent. Second, a chain-extended polysiloxane crosslinker of the invention may be used to improve the surface wettability of a silicone hydrogel lens made from a lens forming material including such chain-extended polysiloxane crosslinker. It is known that a silicone hydrogel material typically has a surface or at least some areas of its surface, which is hydrophobic (non-wettable). Hydrophobic surface or surface areas will up-take lipids or proteins from the ocular environment and may adhere to the eye. Thus, a silicone hydrogel contact lens will generally require a surface modification which is typically carried out after cast-molding of the lens. It is believed that the presence of pendent hydrophilic groups and/or hydrophilic polymer chains along polysiloxane (PDMS) chain may break up the size of hydrophobic domains on lens surface with accessible hydrophilic groups for moisture; and that these hydrophilic groups can be further modified or complexed with other hydrophilic (co)polymer(s) through a simple coating process for enhancing lens surface wettability. Third, a chain-extended polysiloxane crosslinker of the invention can be used to facilitate incorporation of comfort releasing agents for enhancing lens wearing comfort. It is believed that the hydrophilic groups of a chain-extended polysiloxane crosslinker of the invention can bind hydrophilic polymer through hydrogen bonds. For example, the carboxylic acid groups of a chain-extended polysiloxane crosslinker of the invention can build good networking with a polyvinylpyrrolidone homopolymer or copolymer which can be potentially used as comfort agent. For the hydrogen bonded comfort agent(s), the releasing time can be delayed with control according to the binding of comfort agent with a chain-extended polysiloxane crosslinker of the invention. Fourth, a chain-extended polysiloxane crosslinker of the invention may be used to improve lens extraction efficiency, especially by water or an aqueous solution. Extraction of non-volatile residuals from lenses fabricated by monomer formulation is generally required to remove unpolymerized ingredients in the lens formulation. For silicone hydrogel lenses, the non-volatile extractables are usually performed using organic solvent due to the solubility of silicone containing extactables which are not fully soluble in aqueous solution. Presence of pendent hydrophilic groups along the PDMS chain may also enhance the solubility of extractables in aqueous solution in which the organic solvent can be minimized or even eliminated in extraction process.

The present invention, in one aspect, provides a linear polymerizable chain-extended polysiloxane crosslinker which comprises: (1) at least two polysiloxane segments, wherein each pair of adjacent polysiloxane segments is linked by one divalent organic radical which includes at least one pendant hydrophilic groups (hydroxyl and/or carboxyl groups) and a di-thioether linkage —S-DR-S— in which DR is a divalent organic radical; and (2) two terminal ethylenically unsaturated groups.

In accordance with the invention, the chain-extended polysiloxane crosslinker is preferably defined by formula (I)

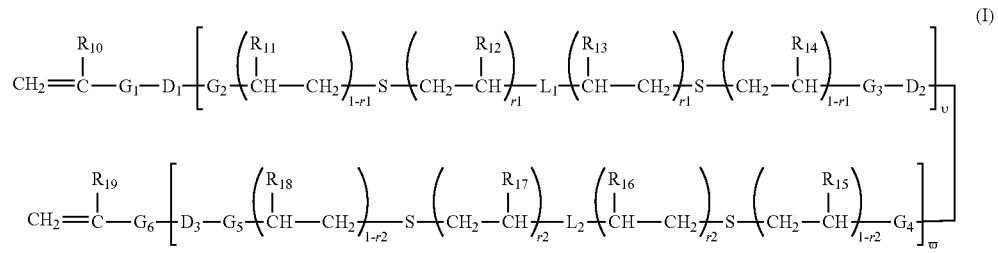

in which
v and ω independent of each other are an integer of from 0 to 20 provided that (v+ω) is an integer of 1 to 20,
$D_1$, $D_2$ and $D_3$ independently of one other are a divalent group of formula (II)

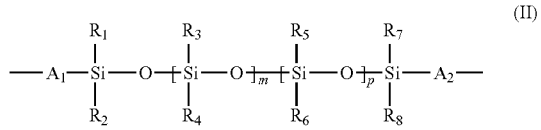

in which $A_1$ and $A_2$ independent of each other are a direct bond, a linear or branched $C_1$-$C_{10}$ alkylene divalent radical, —(CH(R")CH$_2$O)$_{r3}$—CH(R")CH$_2$— in which R" is H or methyl and r3 is an integer of 1 to 20, or a $C_1$-$C_7$ alkyleneoxy $C_1$-$C_7$ alkylene divalent radical, and $R_1$, $R_2$, $R_3$, $R_4$, $R_5$, $R_6$, $R_7$, and $R_8$, independently of one another, are $C_1$-$C_8$-alkyl, $C_1$-$C_4$ alkyl- or $C_1$-$C_4$-alkoxy-substituted phenyl, fluoro($C_1$-$C_{19}$-alkyl), -alk-(OCH$_2$CH$_2$)$_n$—OR$_9$ in which alk is $C_1$-$C_6$-alkylene divalent radical, $R_9$ is $C_1$-$C_6$ alkyl and n is an integer from 1 to 20, m and p independently of each other are an integer of from 0 to 150 and (m+p) is from 1 to 150;

$G_1$, $G_2$, $G_3$, $G_4$, $G_5$, and $G_6$ independent of each other are a direct bond or a divalent radical of formula (III)

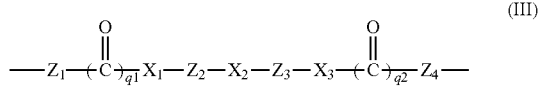

$L_1$ and $L_2$ independent of each other are a direct bond or a divalent radical of formula (IV)

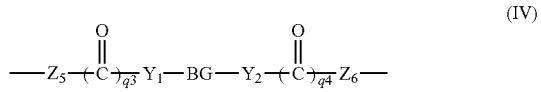

$X_1$, $X_2$, and $X_3$ independent of one other are a linkage selected from the group consisting of a direct bond, —O—, —NR'—, —S—, —C(O)—NR'—, —NR"—C(O)—, —O—C(O)—NH—, —C(O)—O—, —O—C(O)—, —NH—C(O)—O—, —NR'—C(O)—NH—, and —NH—C(O)—NR'—, in which R' is H or $C_1$-$C_8$ alkyl;

$r_1$, $r_2$, $q_1$, $q_2$, $q_3$, and $q_4$ independent of one another are an integer of 0 or 1;

$Y_1$ and $Y_2$ independent of each other are a direct bond, —O— or —NR'— with R' as defined above;

$Z_1$, $Z_2$, $Z_3$, $Z_4$, $Z_5$, $Z_6$, and BG independent of one other are a direct bond, a linear or branched $C_1$-$C_{12}$ alkylene divalent radical, a linear or branched $C_3$-$C_7$ alkylene divalent radical having at least one hydroxyl or carboxyl group or —OC(O)(CH$_2$)$_{t1}$COOH in which t1 is an integer of 2 to 4, a $C_1$-$C_7$ alkyleneoxy $C_1$-$C_7$ alkylene divalent radical, a divalent radical of —[CH$_2$CH(T)CH$_2$O]$_{r4}$—[CH(R")CH$_2$O]$_{r3}$—[CH$_2$CH(T)CH$_2$]$_{r5}$— in which R" and r3 are as defined above, T is hydroxyl or carboxyl group or —OC(O)(CH$_2$)$_t$COOH with t as defined above, and r4 and r5 independent of each other are 0 or 1, an unsubstituted phenylene divalent radical, $C_1$-$C_4$ alkyl or $C_1$-$C_4$ alkoxy substituted phenylene divalent radical or $C_7$-$C_{12}$ arakylene divalent radical, a $C_5$-$C_{45}$ cycloaliphatic or aliphatic-cycloaliphatic divalent radical, a $C_6$-$C_{24}$ aromatic or araliphatic divalent radical, or combinations thereof;

$R_{10}$, $R_{11}$, $R_{12}$, $R_{13}$, $R_{14}$, $R_{15}$, $R_{16}$, $R_{17}$, $R_{18}$, and $R_{19}$ independent of one other are hydrogen or $C_1$-$C_4$ alkyl;

provided that either BG and/or at least one of $G_2$, $G_3$, $G_4$, and $G_5$ comprises at least one hydroxyl or carboxyl group or at least one radical of —OC(O)(CH$_2$)$_{t1}$COOH with t1 as defined above.

In formula (IV), BG is preferably a linear or branched $C_3$-$C_7$ alkylene divalent radical having at least one hydroxyl or carboxyl group or —OC(O)(CH$_2$)$_{t1}$COOH in which t1 is an integer of 2 to 4, a divalent radical of —[CH$_2$CH(T)CH$_2$O]$_{r4}$—[CH(R")CH$_2$O]$_{r3}$—[CH$_2$CH(T)CH$_2$]$_{r5}$— in which R" and r3 are as defined above, T is hydroxyl or carboxyl group or —OC(O)(CH$_2$)$_t$COOH with t as defined above, and r4 and r5 independent of each other are 0 or 1, or a combination thereof. BG can be derived from a dimercaptan or a crosslinking agent comprising at least one hydroxy or carboxyl group or —OC(O)(CH$_2$)$_{t1}$COOH in which t1 is an integer of 2 to 4. It is understood that a hydroxyl group can be readily coverted into —OC(O)(CH$_2$)$_{t1}$COOH by reacting a diacid anhydride (any one described below) with the hydroxyl group.

In formula (II), $R_1$, $R_2$, $R_3$, $R_4$, $R_5$, $R_6$, $R_7$, and $R_8$ preferably are methyl.

In accordance with the invention, a chain-extended polysiloxane crosslinker of the invention can be obtained by either (1) reacting at least one polysiloxane crosslinker (i.e., having one sole polysiloxane segment and two ethylenically-unsaturated groups) with at least one dimercaptan (i.e., a compound having two thiol groups), or (2) reacting at least one di-thiol (or di-mercapto) terminated polysiloxane having one sole polysiloxane segment with at least one crosslinking agent (i.e., a compound having two ethylenicallynically unsaturated groups and a molecular weight of 700 Daltons or less), under Michael Addition or thiol-ene reaction conditions, provided that at least one of the dimercaptan and the polysiloxane crosslinker and at least one of the di-thiol-terminated polysiloxane and the crosslinking agent comprise at least one, preferably at least two, hydrophilic groups selected from the group consisting of hydroxyl group, carboxyl group, and combinations thereof.

A chain-extended polysiloxane crosslinker of the invention can be prepared in a one-pot reaction. For example, a polysiloxane crosslinker can react with a dimercaptan under Michael Addition or thiol-ene reaction conditions at a molar equivalent ratio of about 2:1 to form a prepolymer having two polysiloxane segments linked together through an organic linker including a dioether linkage derived from the dimercaptan.

Alternatively, steps-wise reactions can be used in the preparation of a chain-extended polysiloxane crosslinker of the invention. For example, in the first step, a dimercaptan (or di-thiol-terminated polysiloxane) can be reacted with a polysiloxane crosslinker (or a crosslinking agent) under the Michael Addition or thio-ene reaction conditions at a molar equivalent ratio of about 2:1 or higher to form a thiol-capped polysiloxane having one sole polysiloxane segment (or a thiol-capped chain extended polysiloxane having two polysiloxane segments). In the second step, a polysiloxane crosslinker (or a crosslinking agent) can react with the resultant thiol-capped polysiloxane under the Michael Addition or thio-ene reaction conditions at a molar equivalent ratio of about 2:1 or higher to form a chain-extended polysiloxane crosslinker of the invention having three (or two) polysiloxane segments. Addition step(s) of reactions can be used to add additional polysiloxane segments in a chain-extended polysiloxane crosslinker of the invention.

Any dimercaptans having 2 to 24 carbon atoms can be used in the invention to prepare a prepolymer of the invention. Examples of dimercaptans include without limitation $C_2$-$C_{12}$ alkyl dimercaptans (e.g., ethyl dimercaptan, propyl dimercaptan, butyl dimercaptan, pentamethylen dimercaptan, hexamethylene dimercaptan, heptamethylene dimercaptan, octamethylen dimercaptan, nonamethylene dimercaptan, decamethylene dimercaptan, or combinations thereof), ethylcyclohexyl dimercaptan, dipentene dimercaptan, benzenedithiol, methyl-substituted benzenedithiol, benzenedimethanethiol, glycol dimercaptoacetate, ethyl ether dimercaptan (diglycol dimercaptan), triglycol dimercaptan, tetraglycol dimercaptan, dimercaprol, dimercaptopropanol, dimercaptobutanol, dimercaptopentanol, dimercaptopropionic acid, dihydrolipoic acid, dithiothreitol, dimercaptosuccinic acid, and combinations thereof.

Preferably, a polysiloxane crosslinker used in the preparation of a chain-extended polysiloxane crosslinker is defined by formula (2)

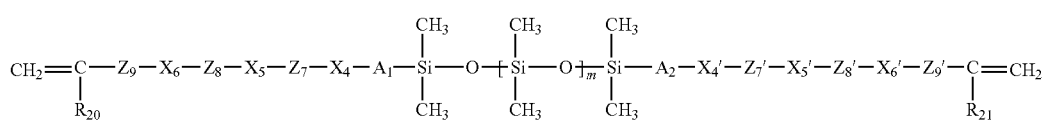

(2)

in which $R_{20}$ and $R_{21}$ independent of each other are hydrogen or methyl; $A_1$ and $A_2$ independent of each other are a direct bond, a linear or branched $C_1$-$C_{10}$ alkylene divalent radical, —(CH(R")CH$_2$O)$_{r3}$—CH(R")CH$_2$— in which R" is H or methyl and r3 is an integer of 1 to 20, or a $C_1$-$C_7$ alkyleneoxy $C_1$-$C_7$ alkylene divalent radical; m is an integer of from 1 to 150; $X_4$, $X_4'$, $X_5$, $X_5'$, $X_6$, and $X_6'$ independent of one other are a linkage selected from the group consisting of a direct bond, —O—, —NR'—, —S—, —C(O)—NR'—, —NR"—C(O)—, —O—C(O)—NH—, —NH—C(O)—O—, —NR'—C(O)—NH—, —NH—C(O)—NR'—, —C(O)—O—, and —O—C(O)—, in which R' is H or $C_1$-$C_8$ alkyl, $Z_7$, $Z_7'$, $Z_8$, $Z_8'$, $Z_9$, and $Z_9'$ independent of one another are a direct bond, a linear or branched $C_1$-$C_{12}$ alkylene divalent radical, a linear or branched $C_3$-$C_7$ alkylene divalent radical having at least one hydroxyl or —OC(O)(CH$_2$)$_{t1}$COOH in which t1 is an integer of 2 to 4, a $C_1$-$C_7$ alkyleneoxy $C_1$-$C_7$ alkylene divalent radical, a divalent radical of —[CH$_2$CH(T)CH$_2$O]$_{r4}$—[CH(R")CH$_2$O]$_{r3}$—[CH$_2$CH(T)CH$_2$]$_{r5}$— in which R" and r3 are as defined above, T is hydroxyl or —OC(O)(CH$_2$)$_1$COOH with t as defined above, and r4 and r5 independent of each other are 0 or 1, an unsubstituted phenylene divalent radical, $C_1$-$C_4$ alkyl or $C_1$-$C_4$ alkoxy substituted phenylene divalent radical or $C_7$-$C_{12}$ arakylene divalent radical, a $C_5$-$C_{45}$ cycloaliphatic or aliphatic-cycloaliphatic divalent radical, a $C_6$-$C_{24}$ aromatic or araliphatic divalent radical, or combinations thereof.

Various polysiloxane crosslinkers of formula (2) (e.g., those terminated with two (meth)acryloyl, allyl, vinyl groups) can be obtained from commercial suppliers (e.g., from Gelest, Inc, or Fluorochem). Examples of such commercially available polysiloxane linkers include without limitation α,ω-di-vinyl terminated polydimethylsiloxane, α,ω-bis[3-(meth)acryloxypropyl]-terminated polydimethylsiloxane, α,ω-bis[3-(meth)acryloxy-2-hydroxypropyloxypropyl]-terminated polydimethylsiloxane, α,ω-bis[3-allyloxy-2-hydroxypropyloxypropyl]-terminated polydimethylsiloxane, and combinations thereof. Otherwise, one skilled in the art will know how to prepare di-ethylenically-unsaturated group-terminated polysiloxanes according to procedures known in the art and described in Journal of Polymer Science—Chemistry, 33, 1773 (1995) (herein incorporated by reference in its entirety).

Alternatively, a polysiloxane crosslinker of formula (2) can be obtained by ethylenically functionalizing a functional polysiloxane (i.e., a polysiloxane terminated with two functional groups selected from the group consisting of amino (—NHR'), hydroxyl, carboxyl, epoxy, isocyanate, anhydride, and combinations thereof), based on a known coupling reaction.

An "ethylenically functionalizing vinylic monomer" refers to a vinylic monomer having one reactive functional group capable of participating in a coupling (or crosslinking) reaction known to a person skilled in the art.

A "coupling reaction" is intended to describe any reaction between a pair of matching functional groups in the presence or absence of a coupling agent to form covalent bonds or linkages under various reaction conditions well known to a person skilled in the art, such as, for example, oxidation-reduction conditions, dehydration condensation conditions, addition conditions, substitution (or displacement) conditions, Diels-Alder reaction conditions, cationic crosslinking conditions, ring-opening conditions, epoxy hardening conditions, and combinations thereof.

Non-limiting examples of coupling reactions under various reaction conditions between a pair of matching co-reactive functional groups selected from the group preferably consisting of amino group (—NHR' as defined above), hydroxyl group, carboxyl group, acid halide group (—COX, X=Cl, Br, or I), acid anhydrate group, aldehyde group, azlactone group, isocyanate group, epoxy group, aziridine group, and thiol group, are given below for illustrative purposes. An amino group reacts with aldehyde group to form a Schiff base which may further be reduced; an amino group —NHR' reacts with an acid chloride or bromide group or with an acid anhydride group to form an amide linkage (—CO—NR'—); an amino group —NHR' reacts with an isocyanate group to form a urea linkage (—NR"—C(O)—NH—); an amino group —NHR' reacts with an epoxy or aziridine group to form an amine bond (—C—NR'—); an amino group —NHR' reacts (ring-opening) with an azlactone group to form an alkylene-diamido linkage (—C(O)NH-alkylene-C(O)NR'—); an amino group —NHR' reacts with a carboxylic acid group in the presence of a coupling agent—carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) to form an amide linkage; a hydroxyl reacts with an isocyanate to form a urethane linkage; a hydroxyl reacts with an epoxy or aziridine to form an ether linkage (—O—); a hydroxyl reacts with an acid chloride or bromide group or with an acid anhydride group to form an ester linkage; an hydroxyl group reacts with an azlactone group in the presence of a catalyst to form an amidoalkylenecarboxy linkage (—C(O)NH-alkylene-C(O)—O—); a carboxyl group reacts with an epoxy group to form an ester bond; a thiol group (—SH) reacts with an isocyanate to form a thiocarbamate linkage (—N—C(O)—S—); a thiol group reacts with an epoxy or aziridine to form a thioether linkage (—S—); a thiol group reacts with an acid chloride or bromide group or with an acid anhydride group to form a thiolester linkage; a thiol group reacts with an azlactone group in the presence of a catalyst to form a linkage (—C(O)NH—$CR_3R_4$—$(CH_2)p$-C(O)—S—). A thiol group reacts with a vinyl group based on thiol-ene reaction under thiol-ene reaction conditions to form a thioether linkage (—S—). A thiol group reacts with an acryloyl or methacryloyl group based on Michael Addition under appropriate reaction conditions to form a thioether linkage.

It is also understood that coupling agents with two reactive functional groups may be used in the coupling reactions. A coupling agent having two reactive functional groups can be a diisocyanate, a di-acid halide, a di-carboxylic acid compound, a di-acid halide compound, a di-azlactone compound, a di-epoxy compound, a diamine, or a diol. A person skilled in the art knows well to select a coupling reaction (e.g., anyone described above in this application) and conditions thereof to prepare a polysiloxane terminated with one or more ethylenically unsaturated groups. For example, a diisocyanate, di-acid halide, di-carboxylic acid, di-azlactone, or di-epoxy compound can be used in the coupling of two hydroxyl, two amino groups, two carboxyl groups, two epoxy groups, or combination thereof; a diamine or dihydroxyl compound can be used in the coupling of two isocyanate, epoxy, aziridine, carboxylic acid, acid halide or azlactone groups or combinations thereof.

Any suitable $C_4$-$C_{24}$ diisocyanates can be used in the invention. Examples of preferred diisocyanates include without limitation isophorone diisocyanate, hexamethyl-1,6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyanto methyl)cyclohexane, cyclohexane diisocyanate, and combinations thereof.

Any suitable diamines can be used in the invention. An organic diamine can be a linear or branched $C_2$-$C_{24}$ aliphatic diamine, a $C_5$-$C_{24}$ cycloaliphatic or aliphatic-cycloaliphatic diamine, or a $C_6$-$C_{24}$ aromatic or alkyl-aromatic diamine. A preferred organic diamine is N,N'-bis(hydroxyethyl)ethylenediamine, N,N'-dimethylethylenediamine, ethylenediamine, N,N'-dimethyl-1,3-propanediamine, N,N'-diethyl-1,3-propanediamine, propane-1,3-diamine, butane-1,4-diamine, pentane-1,5-diamine, hexamethylenediamine, and isophorone diamine.

Any suitable diacid halides can be used in the invention. Examples of preferred diacid halide include without limitations fumaryl chloride, suberoyl chloride, succinyl chloride, phthaloyl chloride, isophthaloyl chloride, terephthaloyl chloride, sebacoyl chloride, adipoyl chloride, trimethyladipoyl chloride, azelaoyl chloride, dodecanedioic acid chloride, succinic chloride, glutaric chloride, oxalyl chloride, dimer acid chloride, and combinations thereof.

Any suitable di-epoxy compounds can be used in the invention. Examples of preferred di-epoxy compounds are neopentyl glycol diglycidyl ether, 1,4-butanediol diglycidyl ether, 1,6-hexanediol diglycidyl ether, glycerol diglycidyl ether, ethylene glycol diglycidyl ether, diethylene glycol diglycidyl ether, polyethylene glycol diglycidyl ether, propylene glycol diglycidyl ether, dipropylene glycol diglycidyl ether, and combinations thereof. Such di-epoxy compounds are available commercially (e.g., those DENACOL series di-epoxy compounds from Nagase ChemteX Corporation).

Any suitable $C_2$-$C_{24}$ diols (i.e., compounds with two hydroxyl groups) can be used in the invention. Examples of preferred diols include without limitation ethylene glycol, diethylene glycol, triethylene glycol, tetraethylene glycol, polyethylene glycol, propylene glycol, 1,4-butanediol, various pentanediols, various hexanediols, various cyclohexanediols, and combination thereof.

Any suitable $C_3$-$C_{24}$ di-carboxylic acid compounds can be used in the invention. Examples of preferred di-carboxylic acid compounds include without limitation a linear or branched $C_3$-$C_{24}$ aliphatic dicarboxylic acid, a $C_5$-$C_{24}$ cycloaliphatic or aliphatic-cycloaliphatic dicarboxylic acid, a $C_6$-$C_{24}$ aromatic or aralphatic dicarboxylic acid, a dicarboxylic acid which contains amino or imido groups or N-heterocyclic rings, and combinations thereof. Examples of suitable aliphatic dicarboxylic acids are: oxalic acid, malonic acid, succinic acid, glutaric acid, adipic acid, pimelic acid, suberic acid, azelaic acid, sebacic acid, undecanedioic acid, dodecanedioic acid, dimethylmalonic acid, octadecylsuccinic acid, trimethyladipic acid, and dimeric acids (dimerisation products of unsaturated aliphatic carboxylic acids, such as oleic acid). Examples of suitable cycloaliphatic dicarboxylic acids are: 1,3-cyclobutanedicarboxylic acid, 1,3-cyclopentanedicarboxylic acid, 1,3- and 1,4-cyclohexanedicarboxylic acid, 1,3- and 1,4-dicarboxylmethylcyclohexane, 4,4'-dicyclohexyldicarboxylic acid. Examples of suitable aromatic dicarboxylic acids are: terephthalic acid, isophthalic acid, o-phthalic acid, 1,3-, 1,4-, 2,6- or 2,7-naphthalenedicarboxylic acids, 4,4'-diphenyldicarboxylic acid, 4,4'-diphenylsulphone-dicarboxylic acid, 1,1,3-trimethyl-5-carboxyl-3-(p-carboxyphenyl)-indane, 4,4'-diphenyl ether-dicarboxylic acid, bis-p-(carboxylphenyl)-methane.

Any suitable $C_{10}$-$C_{24}$ di-azlactone compounds can be used in the invention. Examples of such diazlactone compounds are those described in U.S. Pat. No. 4,485,236 (herein incorporated by reference in its entirety).

The reactions conditions for the above described coupling reactions are taught in textbooks and are well known to a person skilled in the art.

In accordance with the invention, ethylenically functionalizing of a functional polysiloxane can be carried out by covalently attaching ethylenically unsaturated groups to the functional groups (e.g., amine, hydroxyl, carboxyl, isocyanate, anhydride, and/or epoxy groups) of the functional polysiloxane. Any vinylic monomer having a hydroxy, amino, carboxyl, epoxy, aziridine, acid-chloride, isocyanate group, which is coreactive with isocyanate, amine, hydroxyl, carboxy, or epoxy groups of a polysiloxane in the absence or presence of a coupling agent (those described above), can be used in ethylenically functionalizing the polysiloxane. Examples of ethylenically-functionalizing vinylic monomers include without limitation $C_2$ to $C_6$ hydroxylalkyl(meth)acrylate, $C_2$ to $C_6$ hydroxyalkyl (meth)acrylamide, allylalcohol, allylamine, amino-$C_2$-$C_6$ alkyl(meth)acrylate, $C_1$-$C_6$ alkylamino-$C_2$-$C_6$ alkyl(meth)acrylate, vinylamine, amino-$C_2$-$C_6$ alkyl(meth)acrylamide, $C_1$-$C_6$ alkylamino-$C_2$-$C_6$ alkyl (meth)acrylamide, acrylic acid, $C_1$-$C_4$ alkylacrylic acid (e.g., methacrylic ethylacrylic acid, propylacrylic acid, butylacrylic acid), N-[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, aziridinyl $C_1$-$C_{12}$ alkyl(meth)acrylate (e.g., 2-(1-aziridinyl)ethyl(meth)acrylate, 3-(1-aziridinyl) propyl (meth)acrylate, 4-(1-aziridinyl)butyl(meth)acrylate, 6-(1-aziridinyl) hexyl(meth)acrylate, or 8-(1-aziridinyl) octyl (meth)acrylate), glycidyl(meth)acrylate, vinyl glycidyl ether, allyl glycidyl ether, (meth)acrylic acid halide groups (—COX, X═Cl, Br, or I), $C_1$ to $C_6$ isocyanatoalkyl(meth)acrylate, azlactone-containing vinylic monomers (e.g., 2-vinyl-4,4-dimethyl-1,3-oxazolin-5-one, 2-isopropenyl-4,4-dimethyl-1,3-oxazolin-5-one, 2-vinyl-4-methyl-4-ethyl-1,3-oxazolin-5-one, 2-isopropenyl-4-methyl-4-butyl-1,3-oxazolin-5-one, 2-vinyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4-tetramethylene-1,3-oxazolin-5-one, 2-vinyl-4,4-diethyl-1,3-oxazolin-5-one, 2-vinyl-4-methyl-4-nonyl-1,3-oxazolin-5-one, 2-isopropenyl-4-methyl-4-phenyl-1,3-oxazolin-5-one, 2-isopropenyl-4-methyl-4-benzyl-1,3-oxazolin-5-one, 2-vinyl-4,4-pentamethylene-1,3-oxazolin-5-one, and 2-vinyl-4,4-dimethyl-1,3-oxazolin-6-one, with 2-vinyl-4,4-dimethyl-1,3-oxazolin-5-one (VDMO) and 2-isopropenyl-4,4-dimethyl-1,3-oxazolin-5-one (IPDMO) as preferred azlactone-containing vinylic monomers), and combinations thereof.

Various polysiloxanes having two terminal functional groups selected from the group consisting of hydroxyl groups (—OH), amino groups (—NHR'), carboxyl groups (—COOH), epoxy groups, isocyanate groups, thiol groups, and combinations thereof can be obtained from commercial suppliers (e.g., from Gelest, Inc, or Fluorochem). Otherwise, one skilled in the art will know how to prepare such difunctional group-terminated polysiloxanes according to procedures known in the art and described in Journal of Polymer Science—Chemistry, 33, 1773 (1995) (herein incorporated by reference in its entirety).

In a preferred embodiment, a chain-extended polysiloxane crosslinker of the invention is obtained by reacting a dimercaptan with at least one polysiloxane crosslinker of formula (2) in which at least one of $Z_7$, $Z_7'$, $Z_8$, $Z_8'$, $Z_9$, and $Z_9'$ comprises at least one hydroxyl group, based on the mechanism of Michael Addition and/or thiol-ene reaction. Such hydroxy-containing polysiloxane crosslinker can be obtained by ethylenically-functionalizing of: (1) a di-epoxy terminated polysiloxane with use of an ethylenically-functionalizing vinylic monomer selected from the group consisting of $C_2$ to $C_6$ hydroxylalkyl(meth)acrylate, $C_2$ to $C_6$ hydroxyalkyl (meth)acrylamide, allyl alcohol, allylamine, amino-$C_2$-$C_6$ alkyl(meth)acrylate, $C_1$-$C_6$ alkylamino-$C_2$-$C_6$ alkyl(meth)acrylate, vinylamine, amino-$C_2$-$C_6$ alkyl(meth)acrylamide, $C_1$-$C_6$ alkylamino-$C_2$-$C_6$ alkyl(meth)acrylamide, acrylic acid, $C_1$-$C_4$ alkylacrylic acid, N-[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, and combination thereof; (2) a polysiloxane having two terminal functional groups selected from the group consisting of hydroxyl groups, amino groups, carboxyl groups, and combination thereof with use of epoxy-containing vinylic monomer (e.g., glycidyl(meth)acrylate, allyl glycidyl ether, vinyl glycidyl ether, or a combination thereof); (3) a polysiloxane having two terminal functional groups selected from the group consisting of hydroxyl groups, amino groups, carboxyl groups, and combination thereof with use of an ethylenically-functionalizing vinylic monomer selected from the group consisting of $C_2$ to $C_6$ hydroxylalkyl(meth)acrylate, $C_2$ to $C_6$ hydroxyalkyl (meth)acrylamide, allylalcohol, allylamine, amino-$C_2$-$C_6$ alkyl(meth)acrylate, $C_1$-$C_6$ alkylamino-$C_2$-$C_6$ alkyl(meth)acrylate, vinylamine, amino-$C_2$-$C_6$ alkyl(meth)acrylamide, $C_1$-$C_6$ alkylamino-$C_2$-$C_6$ alkyl(meth)acrylamide, acrylic acid, $C_1$-$C_4$ alkylacrylic acid, N-[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, and combination thereof, in the presence of a di-epoxy compound; (4) a di-epoxy-terminated polysiloxane with use of epoxy-containing vinylic monomer (e.g., glycidyl (meth)acrylate, allyl glycidyl ether, vinyl glycidyl ether, or a combination thereof) in the presence of a diol, di-amine compound, di-carboxylic acid compound, or a combination thereof; or (5) combinations thereof.

Examples of preferred hydroxyl-containing polysiloxane crosslinkers include without limitation α,ω-bis[3-(meth)acryloxy-2-hydroxypropyloxypropyl]-terminated polydimethylsiloxane, α,ω-bis[3-(meth)acryloxyethoxy-2-hydroxypropyloxypropyl]-terminated polydimethylsiloxane, α,ω-bis[3-(meth)acryloxyethylamino-2-hydroxypropyloxypropyl]-terminated polydimethylsiloxane, α,ω-bis[3-(meth)acrylamidoethoxy-2-hydroxypropyloxypropyl]-terminated polydimethylsiloxane, α,ω-bis[(meth)acrylamidoethylamino-2-hydroxypropyloxypropyl]-terminated polydimethylsiloxane, α,ω-bis[3-(meth)acryloxypropoxy-2-hydroxypropyloxypropyl]-terminated polydimethylsiloxane, α,ω-bis[3-(meth)acryloxypropylamino-2-hydroxypropyloxypropyl]-terminated polydimethylsiloxane, α,ω-bis[3-(meth)acrylamidopropoxy-2-hydroxypropyloxypropyl]-terminated polydimethylsiloxane, α,ω-bis[3-(meth)acrylamidopropylamino-2-hydroxypropyloxypropyl]-terminated polydimethylsiloxane, α,ω-bis[3-(meth)acrylamidoisopropoxy-2-hydroxypropyloxypropyl]-terminated polydimethylsiloxane, α,ω-bis(allyloxy-2-hydroxypropyl-oxyethoxypropyl)-terminated polydimethylsiloxane, α,ω-bis(allylamino-2-hydroxypropyloxypropyl)-terminated polydimethylsiloxane, α,ω-bis(vinylamino-2-hydroxypropyloxypropyl)-terminated polydimethylsiloxane, α,ω-bis(allyloxy-2-hydroxypropyl-oxypropyl)-terminated polydimethylsiloxane, α,ω-bis(vinyloxy-2-hydroxypropyl-oxyethoxypropyl)-terminated polydimethylsiloxane, α,ω-bis[(meth)acryloxy-2-hydroxypropyloxy-ethoxypropyl]-terminated polydimethylsiloxane, α,ω-bis[(meth)acryloxy-2-hydroxypropyl-N-ethylaminopropyl]-terminated polydimethylsiloxane, α,ω-bis[(meth)acryloxy-2-hydroxypropyl-aminopropyl]-polydimethylsiloxane, α,ω-bis[allyloxy-2-hydroxypropyl-N-ethylaminopropyl]-terminated polydimethylsiloxane, α,ω-bis[vinyloxy-2-hydroxypropyl-N-ethylaminopropyl]-terminated polydimethylsiloxane, α,ω-bis[(meth)acryloxy-2-hydroxypropyl-oxycabonylpropyl]-terminated polydimethylsiloxane, α,ω-bis[allyloxy-2-hydroxypropyl-oxycabonylpropyl]-terminated polydimethylsiloxane, α,ω-bis[vinyloxy-2-hydroxypropyl-oxycabonylpropyl]-terminated polydimethylsiloxane, α,ω-bis[(meth)acryloxy-2-hydroxypropyl-oxypentylcabonyloxyalkyl]-terminated polydimethylsiloxane, α,ω-bis[allyloxy-2-hydroxypropyl-oxy-pentylcabonyloxyalkyl]-terminated polydimethylsiloxane, α,ω-bis[vinyloxy-2-hydroxypropyl-oxy-pentylcabonyloxyalkyl]-terminated polydimethylsiloxane, α,ω-bis(allyloxy-2-hydroxypropyloxy(polyethylenoxy)propyl)-terminated polydimethylsiloxane, α,ω-bis(vinyloxy-2-hydroxypropyl-oxy(polyethylenoxy)propyl)-terminated polydimethylsiloxane, α,ω-bis[(meth)acryloxy-2-hydroxypropyl-oxy(polyethylenoxy)propyl]-terminated polydimethylsiloxane, a coupling product of $C_2$-$C_4$ hydroxyalkyl(meth)acrylate or $C_2$-$C_4$ hydroxyalkyl(meth)acrylamide or (meth)acrylic acid with α,ω-bis(hydroxyethoxypropyl)-polydimethylsiloxane through a di-epoxy compound (e.g., 1,4-butanediol diglycidyl ether, 1,6-hexanediol diglycidyl ether, glycerol diglycidyl ether, ethylene glycol diglycidyl ether, diethylene glycol diglycidyl ether, polyethylene glycol diglycidyl ether, propylene glycol diglycidyl ether, dipropylene glycol diglycidyl ether, or combinations thereof), and combinations thereof.

In another preferred embodiment, a chain-extended polysiloxane crosslinker of the invention is obtained by reacting a dimercaptan having at least one, preferably at least two, hydroxyl or carboxyl groups with at least one polysiloxane crosslinker (i.e., having two terminal ethylenically-unsaturated groups and without any hydroxyl group or preferably with at least one hydroxyl group), based on the mechanism of Michael Addition and/or thiol-ene reaction. More preferably, the dimercaptan comprises at least one carboxyl group and the polysiloxane crosslinker is a hydroxy-containing polysiloxane crosslinker.

In another preferred embodiment, a chain-extended polysiloxane crosslinker of the invention is obtained by reacting a di-thiol-terminated polysiloxane with at least one crosslinking agent having at least one, preferably at least two, hydroxyl groups, based on the mechanism of Michael Addition and/or thiol-ene reaction. Examples of hydroxy-containing crosslinking agents include without limitation glycerol dimethacrylate, N,N'-dihydroxyethylene bis(meth)acrylamide, a product of diamine (preferably selected from the group consisting of N,N'-bis(hydroxyethyl)ethylenediamine, N,N'-dimethylethylenediamine, ethylenediamine, N,N'-dimethyl-1,3-propanediamine, N,N'-diethyl-1,3-propanediamine, propane-1,3-diamine, butane-1,4-diamine, pentane-1,5-diamine, hexamethylenediamine, isophorone diamine, and combinations thereof) and epoxy-containing vinylic monomer (preferably selected from the group consisting of glycidyl(meth)acrylate, vinyl glycidyl ether, allyl glycidyl ether, and combinations thereof). The hydroxyl groups of the crosslinking agents can be converted into pendant carboxyl-containing groups by reacting a di-carboxylic acid anhydride at a desired molar equivalent ratio.

Where a chain-extended polysiloxane crosslinker of formula (I) has pendant hydroxyl groups but free of carboxyl groups, all or a fraction of the pendant hydroxyl groups of the chain-extended polysiloxane crosslinker can be converted into pendant carboxyl groups by reacting a di-carboxylic acid anhydride (e.g., succinic acid anhydride, glutaric acid anhydride, adipic acid anhydride, or combination thereof) with the prepolymer at a desired molar equivalent ratio. Similarly, the hydroxyl groups of a polysiloxane with one or more terminal, hydroxyl-containing ethylenically-unsaturated groups can be converted to carboxyl groups by reacting the polysiloxane with a diacid anhydride before being used to prepare a chain-extended polysiloxane crosslinker of the invention.

It should be understood that although various preferred embodiments of the invention may be separately described above, they can be combined in any desirable fashion to arrive at different preferred embodiments of the invention.

A chain-extended polysiloxane of the invention can find use in preparing a soluble, amphiphilic prepolymer including at least two polysiloxane segment separated by an organic linkage having one or more dangling hydrophilic polymer chains, which is another aspect of the invention. A soluble amphiphilic prepolymer of the invention is obtained by reacting a hydrophilic polymer having one sole terminal reactive functional group capable of reacting with hydroxyl or carboxyl groups of a chain-extended polysiloxane crosslinker of the invention, in the presence or absence of a coupling agent, to form an amphiphilic prepolymer having dangling hydrphophilic chains.

Various embodiments of a chain-extended crosslinkers with pendant hydroxyl and/or carboxyl groups are described above and can be used in this aspect of the invention.

Any hydrophilic polymers having one sole reactive functional group selected from the group consisting of amino group, hydroxyl group, acid chloride group, carboxyl group, anhydride, epoxy group, and combinations thereof can be used in the preparation of an amphiphilic prepolymer with dangling hydrophilic polymer chains. Exemplary such hydrophilic polymers include without limitation monofunctional group-terminated poly(ethylene glycol) (PEG), monofunctional group-terminated PEG/PPG block copolymers, monofunctional group-terminated polyalkylacrylamides, monofunctional group-terminated polyalkylmethacrylamides, monofunctional group-terminated polyvinylpyrrolidones, monofunctional group-terminated copolymers of N-vinylpyrrolidone with one or more vinylic monomers free of any reactive functional group (such as, e.g., dialkylaminoalkylacrylate, dialkylaminoalkylmethacrylate, N,N-dialkylacrylamide, N,N-dialkylmethacrylamide, or mixture thereof), monofunctional group-terminated polymer of one or more hydrophilic vinylic monomers free of reactive functional group (other than ethylenuically unsaturated group), and combinations thereof.

Various monofunctional terminated PEGs can be obtained from Shearwater Polymers, Inc. Preferred monofunctional-terminated PEGs are those PEGs with one amino, hydroxyl, acid chloride, or epoxy group at one terminus and a methoxy or ethoxy group at the other terminus.

Monofunctional group-terminated hydrophilic polymers of one or more hydrophilic vinylic monomers free of any reactive functional group (other than ethylenically unsaturated group) can be prepared according to procedures similar to those described in U.S. Pat. No. 6,218,508, herein incorporated by reference in its entirety. For example, one or more hydrophilic vinylic monomer without functional group (i.e., primary amino group, hydroxyl group, isocyanate group, carboxyl group, or epoxy group) and a chain transfer agent (e.g., 2-mercaptoethanol, 2-aminoethanethiol, 2-mercaptopropinic acid, thioglycolic acid, thiolactic acid, or other hydroxymercaptanes, aminomercaptans, or carboxyl-containing mercaptanes) are copolymerized (thermally or actinically) in the presence or absence of an initiator to obtain a monohydroxy-, monocarboxyl-, or monoamine-terminated hydrophilic polymer or copolymer. Generally, the molar ratio of chain transfer agent to that of one or more hydrophilic vinylic monomers is from about 1:5 to about 1:100. The molar ratio of chain transfer agent to the hydrophilic vinylic monomer without functional group (e.g., DMA, NVP) is selected to obtain a polymer or copolymer with a molecular weight of from about 1000 to about 500,000, preferably from about 5000 to about 300,000, more preferably from about 10000 to about 200,000 Daltons. Monoepoxy-, monoisocyanate-, or monoacidchloride-terminated polymers or copolymers of one or more hydrophilic vinylic monomers can be prepared by covalently attaching epoxy, isocyanate, or acidchloride groups to the above-obtained monohydroxy- or monoamine-terminated polymers or copolymers of one or more hydrophilic vinylic monomers according to any known procedures. Use of monofunctional group-terminated hydrophilic polymers with higher molecular weight may ensure that the interfacial film on a silicone hydrogel material or lens made from a prepolymer of the invention has adequate thickness and coverage.

Alternatively, monofunctional group-terminated hydrophilic polymers can be prepared by polymerizing the one or more hydrophilic monomers in the presence of a hydroxyl-, amine-, or carboxyl-containing free radical initiator at a molar ratio of intiator to the hydrophilic monomers of from about 1:30 to about 1:700. Examples of initiators with amine, hydroxyl, or carboxy group are azo initiators, such as, e.g., 2,2'-Azobis{2-[1-(2-hydroxyethyl)-2-imidazolin-2-yl]propane}dihydrochloride, 2,2'-Azobis {2-methyl-N-[1,1-bis(hydroxymethyl)-2-hydroxyethyl]propionamide, 2,2'-Azobis[2-methyl-N-(2-hydroxyethyl)propionamide], or 2,2'-Azobis{2-methyl-N-[2-(1-hydroxybutyl)]propionamide}, 2,2'-Azobis(2-methylpropionamide)dihydrochloride, 2,2'-Azobis[N-(2-carboxyethyl)-2-methylpropionamidine]tetrahydrate, or the likes.

In a preferred embodiment, a chain extended polysiloxane crosslinker of formula (I) in which $L_1$ and $L_2$ comprises at least one carboxyl group and G2 to G5 is free of any hydroxyl group or preferably comprise at least one hydroxyl group is reacted with a hydrophilic polymer having one sole amino group in the presence of a carbodiimide as a coupling agent to form an amphiphilic prepolymer having dangling hydrophilic polymer chains and pendant hydroxyl groups.

An amphiphilic prepolymer with dangling hydrophilic polymer chains of the invention can be used to prepare silicon hydrogel contact lenses with high oxygen permeability and a hydrophilic surface without post-curing surface treatment. It is believed that when a solution of a prepolymer of the invention is introduced in a mold for making contact lenses, the dangling hydrophilic polymer chains of the prepolymer is preferably adsorbed at the interface between the mold and the prepolymer solution. Where the dangling hydrophilic polymer chains is present in the prepolymer in an amount sufficient, an interfacial films, which is composed essentially of dangling hydrophilic polymer chains and has adequate thickness, can be formed at the mold-solution interface prior to curing (polymerization) and subsequently preserved after curing. As such, one can make a silicone hydrogel contact lens with a hydrophilic interfacial film thereon without any post curing surface treatment.

A chain-extended polysiloxane of the invention can also find use in preparing another soluble, amphiphilic prepolymer comprising: (1) crosslinking units derived from at least one chain-extended polysiloxane crosslinker of the invention and/or an amphiphilic prepolymer having dangling hydrophilic polymer chains; (2) hydrophilic units derived from at least one hydrophilic vinylic monomer as well as at least two ethylenically unsaturated groups; (3) polymerizable units derived from a chain transfer agent and/or vinylic monomer having a reactive functional group and ethylenically unsaturated groups each covalently attached to the polymerizable units through the reactive functional group; (4) optionally hydrophobic units derived from a hydrophobic vinylic monomer; and (5) optionally UV-absorbing units derived from a polymerizable UV-absorbing agent, which is a further aspect of the invention. Such prepolymer of the invention is obtained by first polymerizing a polymerizable composition including (a) a chain-extended polysiloxane crosslinker or an amphiphilic prepolymer having dangling hydrophilic polymer chains of the invention, (b) at least one hydrophilic vinylic monomer, (c) a chain transfer agent with or without a first reactive functional group (other than thiol group) and/or a vinylic monomer having a second reactive functional group (other than ethylenically unsaturated group), (d) optionally a hydrophobic vinylic monomer, and (e) optionally a polymerizable UV-absorbing agent, to form an intermediary copolymer and then by ethylenically functionalizing the intermediary copolymer with an ethylenically functionalizing vinylic monomer having a third reactive functional group capable of reacting with the first or second reactive functional group to form a linkage in a coupling reaction in the presence or absence of a coupling agent to form the prepolymer, wherein the first, second and third reactive functional groups independent of one another are selected from the group consisting of amino group —NHR' with R' as defined above, hydroxyl group, carboxyl group, acid halide group, azlactone group, isocyanate group, epoxy group, aziridine group, and combination thereof. The methods for preparing such amphiphilic prepolymers are disclosed in commonly-owned U.S. Pat. Nos. 6,039,913, 6,043,328, 7,091,283, 7,268,189 and 7,238, 750, 7,521,519; commonly-owned US patent application publication Nos. US 2008-0015315 A1, US 2008-0143958 A1, US 2008-0143003 A1, US 2008-0234457 A1, US 2008-0231798 A1, and commonly-owned U.S. patent application Ser. Nos. 12/313,546, 12/616,166 and 12/616,169; all of which are incorporated herein by references in their entireties.

Any suitable hydrophilic vinylic monomers can be used in this aspect of the invention. Suitable hydrophilic vinylic monomers are, without this being an exhaustive list, hydroxyl-substituted $C_1$-$C_6$ alkyl(meth)acrylates, hydroxyl-substituted $C_1$-$C_6$ alkyl vinyl ethers, $C_1$ to $C_6$ alkyl(meth)acrylamide, di-($C_1$-$C_6$ alkyl) (meth)acrylamide, N-vinylpyrrole, N-vinyl-2-pyrrolidone, 2-vinyloxazoline, 2-vinyl-4,4'-dialkyloxazolin-5-one, 2- and 4-vinylpyridine, olefinically unsaturated carboxylic acids having a total of 3 to 6 carbon atoms, amino-substituted $C_1$-$C_6$ alkyl- (where the term "amino" also includes quaternary ammonium), mono($C_1$-$C_6$ alkyl amino)($C_1$-$C_6$ alkyl) and di($C_1$-$C_6$ alkyl amino)($C_1$-$C_6$ alkyl)(meth)acrylates, allyl alcohol, N-vinyl $C_1$-$C_6$ alkylamide, N-vinyl-N—$C_1$-$C_6$ alkyl amide, and combinations thereof.

Examples of preferred hydrophilic vinylic monomers are N,N-dimethylacrylamide (DMA), N,N-dimethylmethacrylamide (DMMA), 2-acrylamidoglycolic acid, 3-acryloylamino-1-propanol, N-hydroxyethyl acrylamide, N-[tris(hydroxymethyl)methyl]-acrylamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, 2-hydroxyethylmethacrylate (HEMA), 2-hydroxyethyl acrylate (HEA), hydroxypropyl acrylate, hydroxypropyl methacrylate (HPMA), trimethylammonium 2-hydroxy propylmethacrylate hydrochloride, aminopropyl methacrylate hydrochloride, dimethylaminoethyl methacrylate (DMAEMA), glycerol methacrylate (GMA), N-vinyl-2-pyrrolidone (NVP), allyl alcohol, vinylpyridine, a $C_1$-$C_4$-alkoxy polyethylene glycol (meth)acrylate having a weight average molecular weight of up to 1500, methacrylic acid, N-vinyl formamide, N-vinyl acetamide, N-vinyl isopropylamide, N-vinyl-N-methyl acetamide, N-vinyl caprolactam, and mixtures thereof. Among those preferred hydrophilic vinylic monomers, those free of any reactive functional group are particularly preferred for incorporating in the polymerizable composition for preparing the amphiphilic polysiloxane copolymer.

Any suitable hydrophobic vinylic monomers can be used in the preparation of a soluble, amphiphilic prepolymer of the invention. Examples of preferred hydrophobic vinylic monomers include methyl(meth)acrylate, ethyl(meth)acrylate, propyl(meth)acrylate, isopropyl(meth)acrylate, butyl(meth) acrylate, sec-butyl(meth)acrylate, isobutyl (meth)acrylate, t-butyl(meth)acrylate, cyclohexylacrylate, 2-ethylhexylacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate, a silicone-containing vinylic monomer, and mixtures thereof. Most preferably, the polymerizable composition comprises a bulky hydrophobic vinylic monomer. Preferred bulky hydrophobic vinylic monomers include without limitation N-[tris(trimethylsiloxy)silylpropyl]-(meth)acrylamide; N-[tris(dimethylpropyl-siloxy)silylpropyl](meth)acrylamide; N-[tris(dimethylphenylsiloxy)-silylpropyl](meth)acrylamide; N-[tris (dimethylethylsiloxy)silylpropyl](meth)acrylamide; N-(2-hydroxy-3-(3-(bis(trimethyl-silyloxy)methylsilyl) propyloxy)propyl)-2-methyl acrylamide; N-(2-hydroxy-3-(3-(bis(trimethyl-silyloxy)methylsilyl)propyloxy)propyl) acrylamide; N,N-bis[2-hydroxy-3-(3-(bis(trimethylsilyloxy) methylsilyl)propyloxy)propyl]-2-methyl acrylamide; N,N-bis[2-hydroxy-3-(3-(bis(trimethyl-silyloxy)methylsilyl) propyloxy)propyl]acrylamide; N-(2-hydroxy-3-(3-(tris (trimethylsilyloxy)silyl)-propyloxy)propyl)-2-methyl acrylamide; N-(2-hydroxy-3-(3-(tris(trimethylsilyloxy)silyl) propyloxy)-propyl)acrylamide; N,N-bis[2-hydroxy-3-(3-(tris(trimethylsilyloxy)silyl)propyloxy)propyl]-2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl)propyloxy) propyl]acrylamide; N,N-bis[2-hydroxy-3-(3-(t-butyldimethylsilyl)-propyloxy)propyl]-2-methyl acrylamide; N,N-bis[2-hydroxy-3-(3-(t-butyldimethylsilyl) propyloxy)-propyl]acrylamide; 3-methacryloxy propylpentamethyldisiloxane; tris(trimethylsilyloxy)silylpropyl methacrylate (TRIS); (3-methacryloxy-2-hydroxypropyloxy) propylbis(trimethylsiloxy)-methylsilane; (3-methacryloxy-2-hydroxypropyloxy)propyltris(trimethylsiloxy)silane; 3-methacryloxy-2-(2-hydroxyethoxy)-propyloxy)propylbis (trimethylsiloxy)methylsilane; N-2-methacryloxyethyl-O-(methyl-bis-trimethylsiloxy-3-propyl)silyl carbamate; 3-(trimethylsilyl)-propylvinyl carbonate; 3-(vinyloxycarbonylthio)propyl-tris(trimethyl-siloxy)silane; 3-[tris(trimethylsiloxy)silyl]propylvinyl carbamate; 3-[tris(trimethylsiloxy)silyl]propyl allyl carbamate; 3-[tris (trimethylsiloxy)silyl]propyl vinyl carbonate; t-butyldimethyl-siloxyethyl vinyl carbonate; trimethylsilylethyl vinyl carbonate; trimethylsilylmethyl vinyl carbonate; t-butyl (meth)acrylate, cyclohexylacrylate, isobornyl methacrylate, a polysiloxane-containing vinylic monomer (having 3 to 8 silicone atoms), and combinations thereof.

It is believed that the presence of such bulky hydrophobic vinylic monomer in a prepolymer to be used as one of lens forming materials may be able to minimize or eliminate optical defects (permanent deformations) derived from handling during manufacturing in lenses made from the lens-forming materials. Such deformation or optical defect refers to permanent folding marks observed on the lens by a Contact Lens Optical Quality Analyzer (CLOQA) after the lens is folded manually as described in Example 1 of copending U.S. patent application Ser. No. 12/456,364 (herein incorporated by reference in its entirety). It is believed that when a bulky hydrophobic vinylic monomer is present, resultant lenses exhibit a 'healing' effect that eliminated the optical defects (i.e., the folding marks become transient and can disappear after a short time period, e.g., about 15 minutes or less).

Any polysiloxane-containing vinylic monomers and crosslinkers can be used in the invention. A polysiloxane-containing vinylic monomer or crosslinker can be obtained from commercial sources or be prepared according to any known procedures. Examples of preferred polysiloxane-containing vinylic monomers and crosslinkers include without limitation mono-(meth)acrylate-terminated polydimethylsiloxanes of various molecular weight (e.g., mono-3-methacryloxypropyl terminated, mono-butyl terminated polydimethylsiloxane or mono-(3-methacryloxy-2-hydroxypropyloxy) propyl terminated, mono-butyl terminated polydimethylsiloxane); mono-vinyl-terminated, mono-vinyl carbonate-terminated or mono-vinyl carbamate-terminated polydimethylsiloxanes of various molecular weight; di-(meth)acrylated polydimethylsiloxanes (or so called polysiloxane crosslinkers) of various molecular weight; di-vinyl carbonate-terminated polydimethylsiloxanes (polysiloxane crosslinkers); di-vinyl carbamate-terminated polydimethylsiloxane (polysiloxane crosslinkers); di-vinyl terminated polydimethylsiloxanes (polysiloxane crosslinkers); di-(meth)acrylamide-terminated polydimethylsiloxanes (polysiloxane crosslinkers); bis-3-methacryloxy-2-hydroxypropyloxypropyl polydimethylsiloxane (polysiloxane crosslinker); N,N,N',N'-tetrakis(3-methacryloxy-2-hydroxypropyl)-alpha,omega-bis-3-aminopropyl-polydimethylsiloxane (polysiloxane crosslinkers); polysiloxanylalkyl (meth)acrylic monomers; the reaction products of glycidyl methacrylate with amino-functional polydimethylsiloxanes; hydroxyl-containing polysiloxane vinylic monomers or crosslinkers; polysiloxane-containing crosslinkers disclosed in U.S. Pat. Nos. 4,136,250, 4,153,641, 4,182,822, 4,189,546, 4,343,927, 4,254,248, 4,259,467, 4,260,725, and 4,261,875, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, and 6,762,264 (here incorporated by reference in their entireties); di- and tri-block macromers consisting of polydimethylsiloxane and polyalkyleneoxides (e.g., methacrylate end capped polyethyleneoxide-block-polydimethylsiloxane-block-polyethyleneoxide); and mixtures thereof.

Preferred polymerizable UV absorbing agents include without limitation 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl)benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxyethylphenyl)benzotriazole, 2-(2'-hydroxy-5'-methacryloxypropylphenyl)benzotriazole, 2-hydroxy-4-acryloxy alkoxy benzophenone, 2-hydroxy-4-methacryloxy alkoxy benzophenone, allyl-2-hydroxybenzophenone, 2-hydroxy-4-methacryloxy benzophenone. A polymerizable UV-absorbing agent is generally is present in the polymerizable composition for preparing a polysiloxane copolymer which is ethylenically functionalized in turn to obtain a polysiloxane prepolymer of the invention in an amount sufficient to render a contact lens, which is made from a lens forming material including the prepolymer and which absorbs at least about 80 percent of the UV light in the range of from about 280 nm to about 370 nm that impinges on the lens. A person skilled in the art will understand that the specific amount of UV-absorbing agent used in the polymerizable composition will depend on the molecular weight of the UV-absorbing agent and its extinction coefficient in the range from about 280 to about 370 nm. In accordance with the invention, the polymerizable composition comprises about 0.2% to about 5.0%, preferably about 0.3% to about 2.5%, more preferably about 0.5% to about 1.8%, by weight of a UV-absorbing agent.

A chain transfer agent (containing at least one thiol group) is used to control the molecular weight of the resultant intermediary copolymer. Where a chain transfer agent is free of any reactive functional group (other than thiol), a vinylic monomer having a reactive functional group (amine, hydroxyl, carboxyl, epoxy, isocyanate, azlactone, or aziridine group) is present in the polymerizable composition for preparing a prepolymer of the invention. Where a chain transfer has a reactive functional group such as amine, hydroxyl, carboxyl, epoxy, isocyanate, azlactone, or aziridine group, it can provide terminal or pendant functionality (amine, hydroxyl, carboxyl, epoxy, isocyanate, azlactone, or aziridine group) for subsequent ethylenical functionalization of the resultant intermediary copolymer. The vinylic monomer with a reactive functional group can provide another terminal or pendant hydroxyl, carboxyl or amino functionality to the resultant intermediary copolymer.

Generally, the molar ratio of chain transfer agent to that of one or more hydrophilic vinylic monomers is from about 1:5 to about 1:100, whereas the molar ratio of chain transfer agent to the vinylic monomer with a reactive functional group is 1:1. The molar ratio of chain transfer agent to the hydrophilic vinylic monomer without a reactive functional group (e.g., DMA, NVP) is selected to obtain a polymer or copolymer with a molecular weight of preferably from about 200 to about 4,000, more preferably from about 500 to about 2,500 Daltons.

In accordance with the invention, ethylenically functionalizing of an intermediary copolymer can be carried out by covalently attaching ethylenically unsaturated groups to the functional groups (e.g., amine, hydroxyl, carboxyl, isocyanate, and/or epoxy groups) of the intermediary copolymer. Any vinylic monomer having a hydroxy, amino, carboxyl, epoxy, aziridine, acid-chloride, isocyanate group, which is coreactive with isocyanate, amine, hydroxyl, carboxy, or epoxy groups of an intermediary copolymer in the absence or presence of a coupling agent (those described above), can be used in ethylenically functionalizing the polysiloxane. Examples of ethylenically-functionalizing vinylic monomers are those described above and can be used in this embodiment.

The polymerizable composition for preparing an intermediary copolymer can be a melt, a solventless liquid in which all necessary components are blended together, or a solution in which all necessary component is dissolved in an inert solvent (i.e., should not interfere with the reaction between the reactants in the mixture), such as water, an organic solvent, or mixture thereof, as known to a person skilled in the art.

Example of suitable solvents includes without limitation, water, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimethyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methylpyrrolidinone, and mixtures thereof.

The copolymerization of a polymerizable composition for preparing an intermediary copolymer may be induced photochemically or preferably thermally. Suitable thermal polymerization initiators are known to the skilled artisan and comprise, for example peroxides, hydroperoxides, azo-bis (alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis(isobutyronitrile) (AIBN), 1,1-azodiisobutyramidine, 1,1'-azo-bis(1-cyclohexanecarbonitrile), 2,2'-azo-bis(2,4-dimethylvaleronitrile) and the like. The polymerization is carried out conveniently in an above-mentioned solvent at elevated temperature, for example at a temperature of from 25 to 100° C. and preferably 40 to 80° C. The reaction time may vary within wide limits, but is conveniently, for example, from 1 to 24 hours or preferably from 2 to 12 hours. It is advantageous to previously degas the components and solvents used in the polymerization reaction and to carry out said copolymerization reaction under an inert atmosphere, for example under a nitrogen or argon atmosphere. Copolymerization can yield optical clear well-defined copolymers which may be worked up in conventional manner using for example extraction, precipitation, ultrafiltration and the like techniques.

Preferably, an intermediary copolymer comprises: from about 15% to about 70% by weight, preferably from about 25% to about 60%, of crosslinking units derived from at least one chain-extended polysiloxane crosslinker of the invention and/or an amphiphilic prepolymer having dangling hydrophilic polymer chains; from about 10% to about 60%, preferably from about 15% to 45% by weight, of hydrophilic units derived from one or more hydrophilic monomers; from 0 to about 30%, preferably from about 5% to about 25% of bulky hydrophobic units derived from one or more bulky hydrophobic vinylic monomers; and from 0 to about 5%, from about 0.2% to about 4%, preferably about 0.5% to about 2.5%, of a polymerizable UV-absorbing agent. All of the percentages above are weight percents based on the total weight of all polymerizable components including those not listed above.

A chain-extended polysiloxane crosslinker of the invention and a soluble amphiphilic prepolymer of the invention can find particular use in preparing silicone hydrogen ophthalmic lenses, in particular contact lenses.

In a still further aspect, the invention provides a soft contact lens. The soft contact lens of the invention comprises: a silicone hydrogel material that is obtained by curing a lens-forming material in a mold, wherein the lens-forming material comprises chain-extended polysiloxane crosslinker or a soluble amphiphilic prepolymer of the invention (as described above in detail) and one or more components selected from the group consisting of a hydrophilic vinylic monomer, a hydrophobic vinylic monomer, a crosslinking agent having a molecular weight of less than 700 Daltons, a polymerizable UV-absorbing agent, a visibility tinting agent (e.g., dyes, pigments, or mixtures thereof), antimicrobial agents (e.g., preferably silver nanoparticles), a bioactive agent, leachable lubricants, leachable tear-stabilizing agents, and mixtures thereof.

In accordance with the invention, a lens-forming material is a fluid composition, which can be a solution or a melt at a temperature from about 20° C. to about 85° C. Preferably, a lens-forming material is a solution of at least one prepolymer of the invention and other desirable components in water, or an organic solvent, or a mixture of water and one or more organic solvents.

Various embodiments of chain-extended polysiloxane crosslinkers, soluble amphiphilic prepolymers, hydrophilic vinylic monomers, hydrophobic vinylic monomers, solvents, crosslinking agents, polymerizable UV-absorbing agents, photoinitiators are described above and can be used in this aspect of the invention.

Examples of cross-linking agents include without limitation tetraethyleneglycol di-(meth)acrylate, triethyleneglycol di-(meth)acrylate, ethyleneglycol di-(meth)acrylate, diethyleneglycol di-(meth)acrylate, bisphenol A dimethacrylate, vinyl methacrylate, ethylenediamine di(meth)acrylamide, glycerol dimethacrylate, allyl(meth)acrylate, N,N'-methylenebis(meth)acrylamide, N,N'-ethylenebis(meth)acrylamide, N,N'-dihydroxyethylene bis(meth)acrylamide, 1,3-bis(methacrylamidopropyl)-1,1,3,3-tetrakis(trimethylsiloxy)disiloxane, 1,3-bis(N-(meth)acrylamidopropyl)-1,1,3,3-tetrakis-(trimethylsiloxy)disiloxane, 1,3-bis(methacrylamidobutyl)-1,1,3,3-tetrakis(trimethylsiloxy)-disiloxane, 1,3-bis(methacryloxyethylureidopropyl)-1,1,3,3-tetrakis(trimethylsiloxy)disiloxane, a product of diamine (preferably selected from the group consisting of N,N'-bis(hydroxyethyl)ethylenediamine, N,N'-dimethylethylenediamine, ethylenediamine, N,N'-dimethyl-1,3-propanediamine, N,N'-diethyl-1,3-propanediamine, propane-1,3-diamine, butane-1,4-diamine, pentane-1,5-diamine, hexamethylenediamine, isophorone diamine, and combinations thereof) and epoxy-containing vinylic monomer (preferably selected from the group consisting of glycidyl(meth)acrylate, vinyl glycidyl ether, allyl glycidyl ether, and combinations thereof), combinations thereof. A more preferred cross-linking agent to be used in the preparation of a prepolymer of the invention is tetra(ethyleneglycol)diacrylate, tri(ethyleneglycol)diacrylate, ethyleneglycol diacrylate, di(ethyleneglycol)diacrylate, glycerol dimethacrylate, allyl (meth)acrylate, N,N'-methylene bis(meth)acrylamide, N,N'-ethylene bis(meth)acrylamide, N,N'-dihydroxyethylene bis(meth)acrylamide, or combination thereof.

The bioactive agent incorporated in the polymeric matrix is any compound that can prevent a malady in the eye or reduce the symptoms of an eye malady. The bioactive agent can be a drug, an amino acid (e.g., taurine, glycine, etc.), a polypeptide, a protein, a nucleic acid, or any combination thereof. Examples of drugs useful herein include, but are not limited to, rebamipide, ketotifen, olaptidine, cromoglycolate, cyclosporine, nedocromil, levocabastine, lodoxamide, ketotifen, or the pharmaceutically acceptable salt or ester thereof. Other examples of bioactive agents include 2-pyrrolidone-5-carboxylic acid (PCA), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Examples of leachable lubricants include without limitation mucin-like materials (e.g., polyglycolic acid) and non-crosslinkable hydrophilic polymers (i.e., without ethylenically unsaturated groups).

Any hydrophilic polymers or copolymers without any ethylenically unsaturated groups can be used as leachable lubricants. Preferred examples of non-crosslinkable hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methacrylamide, a copolymer of acrylamide or methacrylamide with one or more hydrophilic vinylic monomers, polyethylene oxide (i.e., polyethylene glycol (PEG)), a polyoxyethylene derivative, poly-N—N-dimethylacrylamide, polyacrylic acid, poly 2 ethyl oxazoline, heparin polysaccharides, polysaccharides, and mixtures thereof.

The weight-average molecular weight $M_w$ of the non-crosslinkable hydrophilic polymer is preferably from 5,000 to 500,000, more preferably from 10,000 to 300,000, even more preferably from 20,000 to 100,000.

Examples of leachable tear-stabilizing agents include, without limitation, phospholipids, monoglycerides, diglycerides, triglycerides, glycolipids, glyceroglycolipids, sphingolipids, sphingo-glycolipids, fatty alcohols, fatty acids, mineral oils, and mixtures thereof. Preferably, a tear stabilizing agent is a phospholipid, a monoglyceride, a diglyceride, a triglyceride, a glycolipid, a glyceroglycolipid, a sphingolipid, a sphingo-glycolipid, a fatty acid having 8 to 36 carbon atoms, a fatty alcohol having 8 to 36 carbon atoms, or a mixture thereof.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In a preferred embodiment, reusable molds are used and the lens-forming composition is cured (i.e., polymerized) actinically under a spatial limitation of actinic radiation to form a silicone hydrogel contact lens. Examples of preferred reusable molds are those disclosed in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties. Reusable molds can be made of quartz, glass, sapphire, $CaF_2$, a cyclic olefin copolymer (such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky.), polymethylmethacrylate (PMMA), polyoxymethylene from DuPont (Delrin), Ultem® (polyetherimide) from G.E. Plastics, PrimoSpire®, etc.

In accordance with the invention, the lens-forming composition can be introduced (dispensed) into a cavity formed by a mold according to any known methods.

After the lens-forming composition is dispensed into the mold, it is polymerized to produce a contact lens. Crosslinking may be initiated thermally or actinically, preferably by exposing the lens-forming composition in the mold to a spatial limitation of actinic radiation to crosslink the polymerizable components in the lens-forming composition.

Where the lens-forming composition comprises a polymerizable UV-absorbing agent (i.e., a UV-absorbing moiety-containing vinylic monomer), a benzoylphosphine oxide photoinitiator is preferably used as the photoinitiator in the invention. Preferred benzoylphosphine oxide photoinitiators include without limitation 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. It is understood that any photoinitiators other than benzoylphosphine oxide initiators can be used in the invention.

Opening of the mold so that the molded article can be removed from the mold may take place in a manner known per se.

The molded contact lens can be subject to lens extraction to remove unpolymerized polymerizable components. The extraction solvent can be any solvent known to a person skilled in the art. Examples of suitable extraction solvent are those described above. After extraction, lenses can be hydrated in water or an aqueous solution of a wetting agent (e.g., a hydrophilic polymer).

The molded contact lenses can further subject to further processes, such as, for example, surface treatment (for example, such as, plasma treatment, chemical treatments, the grafting of hydrophilic monomers or macromers onto the surface of a lens, Layer-by-layer coating, etc.); packaging in lens packages with a packaging solution which can contain about 0.005% to about 5% by weight of a wetting agent (e.g., a hydrophilic polymer described above) and/or a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization; and the like.

A contact lens of the invention has an oxygen permeability of preferably at least about 40 barrers, more preferably at least about 55 barrers, even more preferably at least about 70 barrers. In accordance with the invention, an oxygen permeability is an apparent (directly measured when testing a sample with a thickness of, e.g., about 100 microns) oxygen permeability according to procedures described in Examples.

A contact lens of the invention has an elastic modulus of from about 0.1 MPa to about 2.0 MPa, preferably from about 0.2 MPa to about 1.5 MPa, more preferably from about 0.3 MPa to about 1.2 MPa, even more preferably from about 0.4 MPa to about 1.0 MPa.

A contact lens of the invention further has an Ionoflux Diffusion Coefficient, D, of, preferably at least about $1.0 \times 10^{-5}$ mm$^2$/min, more preferably at least about $2.0 \times 10^{-5}$ mm$^2$/min, even more preferably at least about $6.0 \times 10^{-5}$ mm$^2$/min.

A contact lens of the invention further has a water content of preferably from about 15% to about 55%, more preferably from about 20% to about 38% by weight when fully hydrated. The water content of a silicone hydrogel contact lens can be measured according to Bulk Technique as disclosed in U.S. Pat. No. 5,849,811.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together. Therefore, the spirit and scope of the appended claims should not be limited to the description of the preferred versions contained therein.

EXAMPLE 1

Oxygen Permeability Measurements

The apparent oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H. D. Cavanagh Ed., Raven Press: New York 1988, pp 273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm³/min., while a nitrogen stream is passed on the opposite side of the lens at a rate of about 10 to 20 cm³/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The apparent oxygen permeability of the lens material, $Dk_{app}$, is determined from the following formula:

$$Dk_{app} = Jt/(P_{oxygen})$$

where J=oxygen flux [microliters O₂/cm²-minute]
$P_{oxygen} = (P_{measured} - P_{water}$ vapor$) = (\% \; O_2$ in air stream) [mm Hg]=partial pressure of oxygen in the air stream
$P_{measured}$=barometric pressure (mm Hg)
$P_{water}$ vapor=0 mm Hg at 34° C. (in a dry cell) (mm Hg)
$P_{water}$ vapor=40 mm Hg at 34° C. (in a wet cell) (mm Hg)
t=average thickness of the lens over the exposed test area (mm)
$Dk_{app}$ is expressed in units of barrers.

The apparent oxygen transmissibility (Dk/t) of the material may be calculated by dividing the apparent oxygen permeability ($Dk_{app}$) by the average thickness (t) of the lens.

The above described measurements are not corrected for the so-called boundary layer effect which is attributable to the use of a water or saline bath on top of the contact lens during the oxygen flux measurement. The boundary layer effect causes the reported value for the apparent Dk ($Dk_{app}$) of a silicone hydrogel material to be lower than the actual intrinsic Dk value ($Dk_i$). Further, the relative impact of the boundary layer effect is greater for thinner lenses than with thicker lenses. The net effect is that the reported Dk appear to change as a function of lens thickness when it should remain constant.

The intrinsic Dk value of a lens can be estimated based on a Dk value corrected for the surface resistance to oxygen flux caused by the boundary layer effect as follows.

Measure the apparent oxygen permeability values (single point) of the reference Iotrafilcon A (Focus® N&D® from CIBA VISION CORPORATION) or Iotrafilcon B (AirOptix™ from CIBA VISION CORPORATION) lenses using the same equipment. The reference lenses are of similar optical power as the test lenses and are measured concurrently with the test lenses.

Measure the oxygen flux through a thickness series of Iotrafilcon A or Iotrafilcon B (reference) lenses using the same equipment according to the procedure for apparent Dk measurements described above, to obtain the intrinsic Dk value ($Dk_i$) of the reference lens. A thickness series should cover a thickness range of approximately 100 μm or more. Preferably, the range of reference lens thicknesses will bracket the test lens thicknesses. The $Dk_{app}$ of these reference lenses must be measured on the same equipment as the test lenses and should ideally be measured contemporaneously with the test lenses. The equipment setup and measurement parameters should be held constant throughout the experiment. The individual samples may be measured multiple times if desired.

Determine the residual oxygen resistance value, $R_r$, from the reference lens results using equation 1 in the calculations.

$$R_r = \frac{\sum \left( \frac{t_j}{Dk_{app}} - \frac{t_j}{Dk_i} \right)}{n} \quad (1)$$

In which t is the thickness of a reference lens under measurement, and n is the number of the reference lenses measured. Plot the residual oxygen resistance value, $R_r$, vs. t data and fit a curve of the form Y=a+bX where, for the jth lens, $Y_j=(\Delta P/J)_j$ and $X=t_j$. The residual oxygen resistance, $R_r$, is equal to a.

Use the residual oxygen resistance value determined above to calculate the correct oxygen permeability $Dk_c$ (estimated intrinsic Dk) for the test lenses based on Equation 2.

$$Dk_c = t/[(t/Dk_a) - R_r] \quad (2)$$

The estimated intrinsic Dk of the test lens can be used to calculate what the apparent Dk ($Dk_{a\_std}$) would have been for a standard thickness lens in the same test environment based on Equation 3.

$$Dk_{a\_std} = t_{std}/[(t_{std}/Dk_c) + R_{r\_std}] \quad (3)$$

Ion Permeability Measurements.

The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of $0.314 \times 10^{-3}$ mm²/minute.

Water Contact Angle (WCA) Measurements.

Water contact angle (WCA) measurements are performed by the sessile drop method with a DSA 10 drop shape analysis system from Krüss GmbH, Germany with pure water (Fluka, surface tension 72.5 mN/m at 20° C.). For measurement purposes a contact lens is taken off the storage solution with tweezers and excess storage solution is removed by gentle shaking. The contact lens are placed on the male part of a lens mold and gently blotted with a dry and clean cloth. A water droplet (approximately 1 μl) is then dosed on the lens apex, and the change of the contact angle over time of this water droplet (WCA(t), circle fitting mode) is monitored. The WCA is calculated by the extrapolation of the graph WCA(t) to t=0.

UV-Absorbance.

Contact lenses are manually placed into a specially fabricated sample holder or the like which can maintain the shape of the lens as it would be when placing onto eye. This holder is then submerged into a 1 cm path-length quartz cell containing phosphate buffered saline (PBS, pH~7.0-7.4) as the reference. A UV/visible spectrophotometer, such as, Varian Cary 3E UV-Visible Spectrophotometer with a LabSphere DRA-CA-302 beam splitter or the like, can be used in this measurement. Percent transmission spectra are collected at a wavelength range of 250-800 nm with % T values collected at 0.5 nm intervals. This data is transposed onto an Excel spreadsheet and used to determine if the lenses conform to Class 1 UV absorbance. UV absorbance is calculated using the following equations:

$$UVA\ \%\ T = \frac{\text{Average \% } T \text{ between 380-316 nm}}{\text{Luminescence \% } T} \times 100$$

$$UVB\ \%\ T = \frac{\text{Average \% } T \text{ between 280-315 nm}}{\text{Luminescence \% } T} \times 100$$

In which Luminescence % T is the average % transmission between 380 and 780.

EXAMPLE 2

Synthesis of CE-PDMS with OH Groups (CE-PDMS-(OH)x)

A chain-extended polydimethylsiloxane crosslinker with pendant hydroxyl groups is prepared according to the reaction scheme below.

the mixture. After the temperature reaches 40° C., the reaction is maintained at 40° C. for 8 hours. After cooling to room temperature, 1% of the solution is collected for checking residual —SH with iodine titration and no residual —SH is detected. The solution is then acidified with 1 mL of acetic acid and transferred to a separate funnel with additional 250 mL of hexanes. The first extraction is performed with 1000 mL of 20 v % 2-propanol aqueous solution. Additional 200 mL of hexanes and 150 mL of 2-propanol are added to enhance the phase separation. Two additional extractions are performed with 500 mL of 25 v % 2-propanol aqueous solution. The hexanes phase is collected and dried with 10 g $MgSO_4$ for 1 hour. After $MgSO_4$ is removed by filtration, the solution is concentrated to ~113 g. The total solution Wt. is 114.397 g and the solid content for this CE-PDMS-(OH)x solution is 48.2%. The yield is about 97%. The double bond content is 0.185 meq/g.

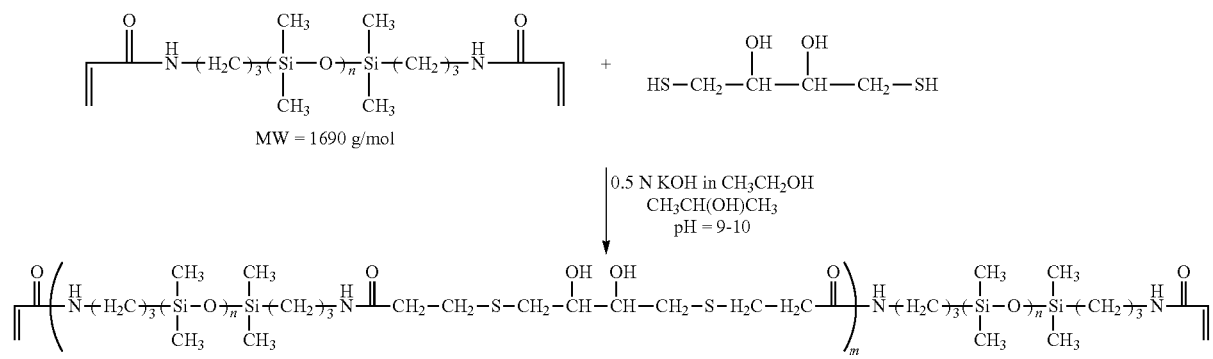

60.70 g of α,ω-bis(acrylamidopropyl) terminated polydimethylsiloxane (1,600 g/mol) solution in hexanes (86.6%), corresponding to 52.48 g of PDMS diacrylamide (32.8 meq), is added in 250 mL of hexane/2-propanol (50/50, v/v) (Solution A). Dithiothreitol (3.90 g, 25.3 meq) is dissolved in 250 mL of hexanes/2-propanol (50:50, v/v) (Solution B). Solution A and solution B are combined in a 1-L 3-neck round bottom flask in the ice bath, which is equipped with a stirring bar and condenser and kept under Nitrogen with a flow of 200 mL/minute. Then 20 mL of 0.5 N KOH in ethanol is added to

EXAMPLE 3

Synthesis of CEPDMS with COOH Groups (CE-PDMS-(COOH)y

A chain-extended polydimethylsiloxane crosslinker with pendant carboxyl groups is prepared according to the reaction scheme below.

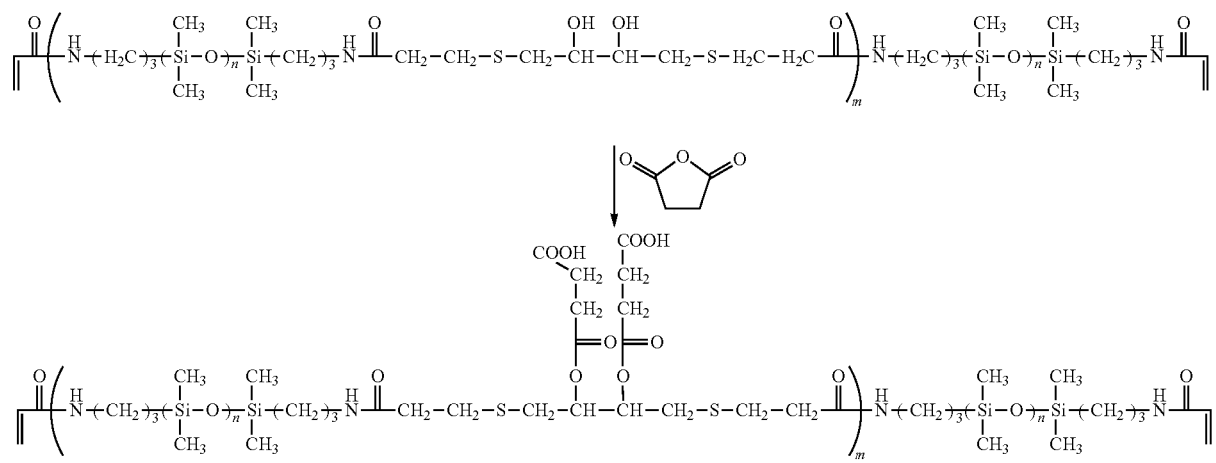

84.90 g of CEPDMS-(OH)x solution in hexanes (54.0%) prepared in Example 2 is added to a 500 mL round bottom flask, followed by addition of 45 g of pyridine. The solution is then concentrated to 91.00 g via rota-yap (Solution A). In a separate flask is succinic anhydride (8.27 g) added, followed by addition of 100 g of pyridine (Solution B). In a 20 mL vial is 1.01 g of 4-N,N'-dimethylamino pyridine dissolved in 10 mL of pyridine (Solution C). After Solution B and Solution C are added to Solution A, additional 100 g of pyridine are charged. This mixture is heated under a slow air flow (~150 mL/minute) at 60° C. for 4 hours. After reaction, the color of the mixture changes to very light brown. After the reaction is cooled to RT, 50 mL of DI water is added, followed by a 60 minutes of stirring. The reaction solution is then transferred to a 1-L separation funnel and then mixed with 400 mL of hexanes, 100 mL of 2-propanol and 250 mL of DI water. After a mild shaking, the phases are slowly separated. Remove the aqueous phase and wash the organic phase with 200 mL of 0.25 N HCl in 25 v % of 2-propanol aqueous solution for 4-5 times until the aqueous becomes acidic. After the last wash, Organic phase is collected and dried with 10 g MgSO$_4$ for 1 hour. After MgSO$_4$ is removed by filtration, the solution is concentrated to 100 g and then diluted with 50 g of 1-propanol. The solution is concentrated to 78.28 g. Based on solid content, 59.49% in 1-PrOH, the yield is 93%. The COOH content is 0.766 meq/g.

EXAMPLE 4

Hydrophilic PDMS with Pendant Jeffamine Chains

A chain-extended polydimethylsiloxane crosslinker with pendant polyethyleneglycol-polypropyleneglycol block copolymer chains is prepared according to the reaction scheme below.

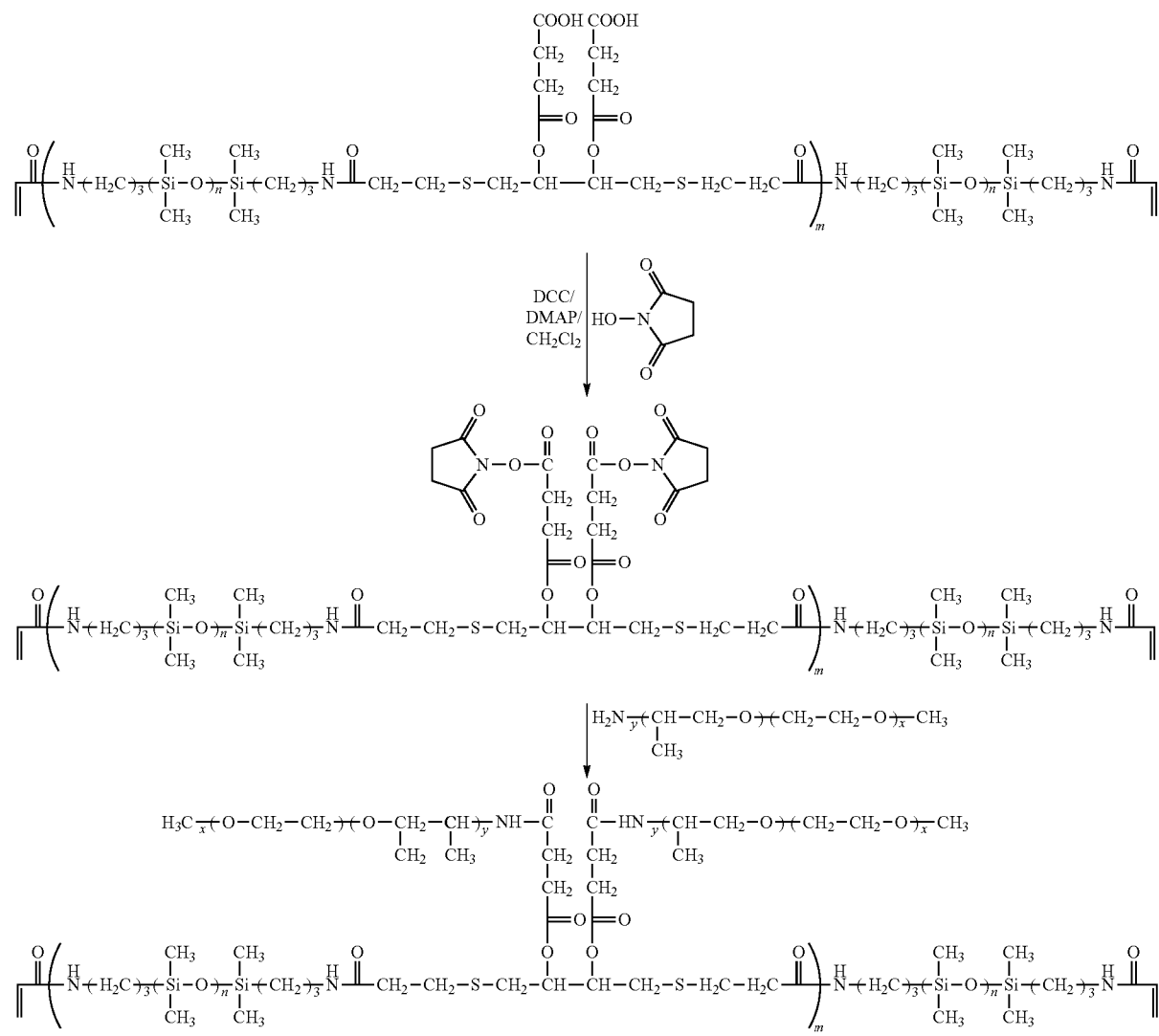

In a 250 mL of round bottom flask added 10 g of above prepared PDMS-(COOH)y (~7.66 meq COOH) prepared in Example 3, 0.98 g of N-hydroxysuccinimide (NHS), followed by addition of a mixture of 50 g of dichloromethane and 5 ml of THF. The solution is well stirred. After the solution is cooled down using the ice bath, 1.58 g (7.66 meq) of N,N'-dicyclohexylcarbodiimide (DCC) dissolved in 5 mL of dichloromethane is added. The reaction is carried out at 0° C. for about 5 minutes and continued for about 2 hours with no ice bath. After the solution is filtered through a 1 μm pore size filter paper to a 250 mL round bottom flask in an ice bath, a solution of mono-amine mono-methyl terminated polyethyleneglycol-polypropyleneglycol block copolymer, Jeffamine 2070, (15 g, 7.1 meq) in 10 g of dichloromethane is drop-wisely via an additional funnel within 1 hour. The reaction continues for 20 hours at room temperature. After removal of majority of the solvent, 80 mL of methanol is added to dilute the solution. The diluted solution is then transferred to a dialysis tube (MWCO, 3,500 Dalton) and underwent dialysis in 2 L of methanol for two days, with change of solvent three times. The solution in the dialysis tube is transferred to a 250 ml round bottom flask and the solvent is removed via rota-yap at 35° C., and further removal of the residual solvent was achieved via high vacuum (5 mbar at 25° C.). 17 g of final product is obtained, with yield of 68%. The average molecular weight (Mn) is 21,958 g/mol based on GPC using PDMS as the standards, while the starting PDMS has GPC measured Mn of 16,061 g/mol.

EXAMPLE 5

Hydrophilic PDMS with Pendant Jeffamine and Alkyl Chains

Example D

In a 250 ml of round bottom flask added 5.9 g (~4.52 meq of COOH) of PDMS-(COOH)y prepared in Example 3, 0.88 g of NHS, followed by a mixture of 50 g of dichloromethane and 5 mL of THF. The solution is well stirred. After the solution is cooled down using the ice bath, 1.58 g (7.66 meq) of DCC in 5 mL of dichloromethane is added. The reaction is carried out at 0° C. for about 5 minutes and continued for about 2 hours with no ice bath. After the solution is filtered through a 1 um pore size filter paper to a 250 mL round bottom flask in an ice bath. The solution of mono-amine mono-methyl terminated polyethyleneglycol-polypropyleneglycol block copolymer, Jeffamine 2070 (5.1 g, 2.55 meq) and 1-dodecacylamine (0.95 g, 5.11 meq) in 10 g of dichloromethane is drop-wisely via an additional funnel within 1 hour. The reaction continues for about 20 hours at room temperature. After removal of majority of the solvent, 80 mL of methanol is added to dilute the solution. The diluted solution is then transferred to a dialysis tube (MWCO, 3,500 Dalton) and underwent dialysis in 2 L of methanol for two days, with change of solvent three times. The solution in the dialysis tube is transferred to a 250 ml round bottom flask and the solvent is removed via rota-yap at 35° C., and further removal of the residual solvent is achieved via high vacuum (5 mbar at 25° C.). 5.7 g of final product is obtained with yield of 48%.

EXAMPLE 6

Hydrophilic PDMS with Pendant Jeffamine and Fluorinated Alkyl Chains

In a 250 ml of round bottom flask added 10 g (~7.66 meq of COOH) of PDMS-(COOH)y prepared in Example 3, 0.88 g of NHS, followed by a mixture of 50 g of dichloromethane and 5 mL of THF. The solution is well stirred. After the solution is cooled down using the ice bath, 1.58 g (7.66 meq) of DCC in 5 mL of dichloromethane is added. The reaction is carried out at 0° C. for 5 minutes and continued for 2 hours with no ice bath. After the solution is filtered through a 1 um pore size filter paper to a 250 mL round bottom flask in an ice bath. The solution of Jeffamine 2070 (5.1 g, 2.55 meq) and 2,2,2-trifluoroethylamine (0.46 g, 5.11 meq) in 10 g of dichloromethane is drop-wisely via an additional funnel within 1 hour. The reaction continues for 20 hours at room temperature. After removal of majority of the solvent, 80 mL of methanol is added to dilute the solution. The diluted solution is then transferred to a dialysis tube (MWCO, 3,500 Dalton) and underwent dialysis in 2 L of methanol for two days, with change of solvent three times. The solution in the dialysis tube is transferred to a 250 ml round bottom flask and the solvent is removed via rota-yap at 35° C., and further removal of the residual solvent is achieved via high vacuum (5 mbar at 25° C.). 12.6 g of final product is obtained with yield of 81%. The double bond content in the final polymer is 0.1233 meq/g.

EXAMPLE 7

Lens Formulation and Lens Casting

Various lens formulations with the compositions shown in the table below are prepared. The homogenization of the mixture is achieved via rolling on the roller overnight. A lens formulation is placed in polypropylene plastic molds under UV light (5.8 mW/cm$^2$) for 5 minutes. After removing the lens from the molds, contact lens is extracted with methyl ethyl ketone for about 5 minutes, followed with DI water for about 5 minutes. The lenses are stored in PBS in the glass vial and autoclaved at 120° C. for 30 minutes.

| Components | Form. A | Form. B | Form. C | Form. D | Form. C | Form. D |
|---|---|---|---|---|---|---|
| Hydrophilized PDMS | 0.55 (Exp. 4) | 0.55 (Exp. 4) | 0.55 (Exp. 5) | 0.55 (Exp. 5) | 0.55 (Exp. 6) | 0.55 (Exp. 6) |
| DMA | 0.11 | 0.10 | 0.11 | 0.10 | 0.11 | 0.10 |
| MBA | 0.01 | 0.01 | 0.01 | 0.01 | 0.01 | 0.01 |
| BA |  | 0.12 |  | 0.12 |  | 0.12 |
| TrisAA | 0.12 |  | 0.12 |  | 0.12 |  |
| DC-1173 | 0.01 | 0.01 | 0.01 | 0.01 | 0.01 | 0.01 |
| 1-propanol | 0.2 | 0.2 | 0.2 | 0.2 | 0.2 | 0.2 |
| Characterization |  |  |  |  |  |  |
| WBUT (Before autoclave) | 0++ | 0++ | 0++ | 12 s | 10 s | 11 s |
| WBUT (After autoclave) | 0+ | 0+ | 0+ | 0+ | 0+ | 0+ |
| Lens haze level | 2 | 2 | 2 | 2 | 0-1 | 0-1 |

Note:
DMA: N,N-dimethyl acrylamide;
MBA: Methylene bisacrylamide;
BA: Butyl acrylate;
Tris: Tris(trimethylsiloxy)propyl acrylamide;
DC-1173: Darocur 1173.
WBUT: Water break-up time between when the lens is taken out from PBS saline and when the water film breaks.
WBUT = 0++: Dry spots on the lens edge and the lens center remains wettable.
WBUT = 0+: Dry spots on the lens edge and some dry spots scatter in on the lens surface, and majority surface remains wettable.
Lens Haze Rating
0 - Clear, no visible haze;
1 - Barely visible, you really have to look hard to see it;
2 - Slightly visible, not easy to see;
3 - Visible, easy to see;
4 - Slightly opaque, almost white (cloudy);
5 - Opaque, very white, not transparent

What is claimed is:

1. A chain-extended polysiloxane crosslinker, being represented by formula (I)

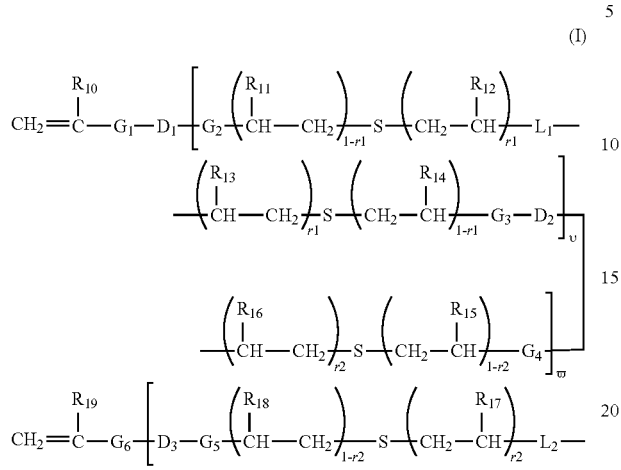

in which:
v and ω independent of each other are an integer of from 0 to 20 provided that (v+ω) is an integer of 1 to 20, $D_1$, $D_2$ and $D_3$ independently of each other are a divalent group of formula (II)

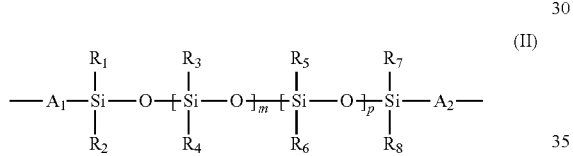

in which $A_1$ and $A_2$ independent of each other are a direct bond, a linear or branched $C_1$-$C_{10}$ alkylene divalent radical, —(CH(R")CH$_2$O)$_{r3}$—CH(R")CH$_2$— in which R" is H or methyl and r3 is an integer of 1 to 20, or a $C_1$-$C_7$ alkyleneoxy $C_1$-$C_7$ alkylene divalent radical, and $R_1$, $R_2$, $R_3$, $R_4$, $R_5$, $R_6$, $R_7$, and $R_8$, independently of $C_1$-$C_4$ alkyl-substituted phenyl, $C_1$-$C_4$-alkoxy-substituted phenyl, fluoro($C_1$-$C_{18}$-alkyl), or -alk-(OCH$_2$CH$_2$)$_n$—OR$_9$— radical, R$_9$ is $C_1$-$C_6$ alkyl and n is an integer from 1 to 20, m and p independently of each other are an integer of from 0 to 150 and (m+p) is from 1 to 150;

$G_1$, $G_2$, $G_3$, $G_4$, $G_5$, and $G_6$ independent of each other are a direct bond or a divalent radical of formula (III)

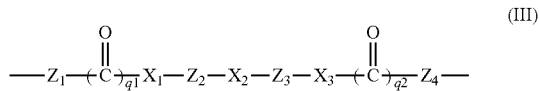

$L_1$ and $L_2$ independent of each other are a direct bond or a divalent radical of formula (IV)

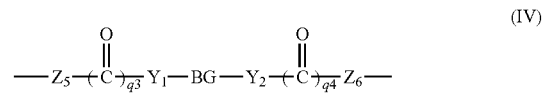

$X_1$, $X_2$, and $X_3$ independent of each other are a linkage selected from the group consisting of a direct bond, —O—, —NR'—, —S—, —C(O)—NR'—, —NR"—C(O)—, —O—C(O)—NH—, —C(O)—O—, —O—C(O)—, —NH—C(O)—O—, —NR'—C(O)—NH—, and —NH—C(O)—NR'—, in which R' is H or $C_1$-$C_8$ alkyl;

$r_1$, $r_2$, $q_1$, $q_2$, $q_3$, and $q_4$ independent of one another are an integer of 0 or 1;

$Y_1$ and $Y_2$ independent of each other are a direct bond, —O— or —NR'— with R' as defined above;

$Z_1$, $Z_2$, $Z_3$, $Z_4$, $Z_5$, $Z_6$, and BG independent of each other are a direct bond, a linear or branched $C_1$-$C_{12}$ alkylene divalent radical, a linear or branched $C_3$-$C_7$ alkylene divalent radical having at least one hydroxyl or carboxyl group or —OC(O)(CH$_2$)$_{t1}$COOH in which t1 is an integer of 2 to 4, a $C_1$-$C_7$ alkyleneoxy $C_1$-$C_7$ alkylene divalent radical, a divalent radical of —[CH$_2$CH(T)CH$_2$O]$_{r4}$—[CH(R")CH$_2$O]$_{r3}$—[CH$_2$CH(T)CH$_2$]$_{r5}$— in which R" and r3 are as defined above, T is a hydroxyl or carboxyl group, and r4 and r5 independent of each other are 0 or 1, an unsubstituted phenylene divalent radical, $C_1$-$C_4$ alkyl substituted phenylene divalent radical, $C_1$-$C_4$ alkoxy substituted phenylene divalent radical, $C_7$-$C_{12}$ aralkylene divalent radical, a $C_5$-$C_{45}$ cycloaliphatic divalent radical, a $C_5$-$C_{45}$ aliphatic-cycloaliphatic divalent radical, a $C_6$-$C_{24}$ aromatic divalent radical, a $C_6$-$C_{24}$ araliphatic divalent radical, or combinations thereof;

$R_{10}$, $R_{11}$, $R_{12}$, $R_{13}$, $R_{14}$, $R_{15}$, $R_{16}$, $R_{17}$, $R_{18}$, and $R_{19}$ independent of each other are hydrogen or $C_1$-$C_4$ alkyl;

provided that BG and/or at least one of $G_2$, $G_3$, $G_4$, and $G_5$ comprises at least one hydroxyl or carboxyl group or at least one radical of —OC(O)(CH$_2$)$_{t1}$COOH with t1 as defined above.

2. The chain-extended polysiloxane crosslinker of claim 1, wherein BG is a linear or branched $C_3$-$C_7$ alkylene divalent radical having at least one hydroxyl or carboxyl group or —OC(O)(CH$_2$)$_{t1}$COOH in which t1 is an integer of 2 to 4, a divalent radical of —[CH$_2$CH(T)CH$_2$O]$_{r4}$—[CH(R")CH$_2$O]$_{r3}$—[CH$_2$CH(T)CH$_2$]$_{r5}$— in which R" and r3 are as defined above, T is a hydroxyl or carboxyl group, and r4 and r5 independent of each other are 0 or 1, or combinations thereof.

3. The chain-extended polysiloxane crosslinker of claim 1, wherein the chain-extended polysiloxane crosslinker is obtained by reacting at least one polysiloxane crosslinker of formula (2) with at least one dimercaptan, under Michael Addition or thiol-ene reaction conditions,

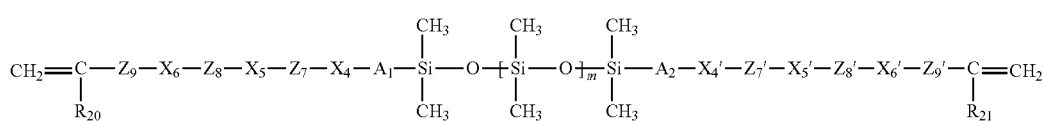

in which $R_{20}$ and $R_{21}$ independent of each other are hydrogen or methyl; $A_1$ and $A_2$ independent of each other are a direct bond, a linear or branched $C_1$-$C_{10}$ alkylene divalent radical, —(CH(R")CH$_2$O)$_{r3}$—CH(R")CH$_2$— in which R" is H or methyl and r3 is an integer of 1 to 20, or a $C_1$-$C_7$ alkyleneoxy $C_1$-$C_7$ alkylene divalent radical; m is an integer of from 1 to 350; $X_4$, $X_4'$, $X_5$, $X_5'$, $X_6$, and $X_6'$ independent of each other are a linkage selected from the group consisting of a direct bond, —O—, —NR'—, —S—, —C(O)—NR'—, —NR"—C(O)—, —O—C(O)—NH—, —NH—C(O)—O—, —NR'—C(O)—NH—, —NH—C(O)—NR'—, —C(O)—O—, and —O—C(O)—, in which R' is H or $C_1$-$C_8$ alkyl, $Z_7$, $Z_7'$, $Z_8$, $Z_8'$, $Z_9$, and $Z_9'$ independent of one another are a direct bond, a linear or branched $C_1$-$C_{12}$ alkylene divalent radical, a linear or branched $C_3$-$C_7$ alkylene divalent radical having at least one hydroxyl or —OC(O)(CH$_2$)$_{t1}$COOH in which t1 is an integer of 2 to 4, a $C_1$-$C_7$ alkyleneoxy $C_1$-$C_7$ alkylene divalent radical, a divalent radical of —[CH$_2$CH(T)CH$_2$O]$_{r4}$—[CH(R")CH$_2$O]$_{r3}$—[CH$_2$CH(T)CH$_2$]$_{r5}$— in which R" and r3 are as defined above, T is a hydroxyl, and r4 and r5 independent of each other are 0 or 1, an unsubstituted phenylene divalent radical, $C_1$-$C_4$ alkyl substituted phenylene divalent radical, $C_1$-$C_4$ alkoxy substituted phenylene divalent radical, $C_7$-$C_{12}$ aralkylene divalent radical, a $C_5$-$C_{45}$ cycloaliphatic divalent radical, a $C_5$-$C_{45}$ aliphatic-cycloaliphatic divalent radical, a $C_6$-$C_{24}$ aromatic divalent radical, a $C_6$-$C_{24}$ araliphatic divalent radical, or combinations thereof.

4. The chain-extended polysiloxane crosslinker of claim 3, wherein said at least one polysiloxane crosslinker comprises at least one hydroxyl group and is obtained by ethylenically-functionalizing of: (1) a di-epoxy terminated polysiloxane with use of an ethylenically-functionalizing vinylic monomer selected from the group consisting of $C_2$ to $C_6$ hydroxylalkyl (meth)acrylate, $C_2$ to $C_6$ hydroxyalkyl (meth)acrylamide, allyl alcohol, allylamine, amino-$C_2$-$C_6$ alkyl (meth)acrylate, $C_1$-$C_6$ alkylamino-$C_2$-$C_6$ alkyl (meth)acrylate, vinylamine, amino-$C_2$-$C_6$ alkyl (meth)acrylamide, $C_1$-$C_6$ alkylamino-$C_2$-$C_6$ alkyl (meth)acrylamide, acrylic acid, $C_1$-$C_4$ alkylacrylic acid, N-[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carboxy-4-phenyl-1,3-butadiene, itaconic acid, citraconic acid, mesaconic acid, glutaconic acid, aconitic acid, maleic acid, fumaric acid, and a combination thereof; (2) a polysiloxane having two terminal function groups selected from the group consisting of hydroxyl groups, amino groups, carboxyl groups, and a combination thereof with use of epoxy-containing vinylic monomer; (3) a polysiloxane having two terminal function groups selected from the group consisting of hydroxyl groups, amino groups, carboxyl groups, and a combination thereof with use of an ethylenically-functionalizing vinylic monomer selected from the group consisting of $C_2$ to $C_6$ hydroxylalkyl (meth)acrylate, $C_2$ to $C_6$ hydroxyalkyl (meth)acrylamide, allylalcohol, allylamine, amino-$C_2$-$C_6$ alkyl (meth)acrylate, $C_1$-$C_6$ alkylamino-$C_2$-$C_6$ alkyl (meth)acrylate, vinylamine, amino-$C_2$-$C_6$ alkyl (meth)acrylamide, $C_1$-$C_6$ alkylamino-$C_2$-$C_6$ alkyl (meth)acrylamide, acrylic acid, $C_1$-$C_4$ alkylacrylic acid, N-[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carboxyl-4-phenyl butadiene-1,3, itaconic acid, citraconic acid, mesaconic acid, glutaconic acid, aconitic acid, maleic acid, fumaric acid, and a combination thereof in the presence of a di-epoxy compound; (4) a di-epoxy-terminated polysiloxane with use of glycidyl(meth)acrylate in the presence of a diol, di-amine compound, di-carboxylic acid compound, or a combination thereof; or (5) combinations thereof.

5. The chain-extended polysiloxane crosslinker of claim 3, wherein said at least one polysiloxane crosslinker is: α,ω-bis[3-(meth)acryloxy-2-hydroxypropyloxypropyl]-terminated polydimethylsiloxane, α,ω-bis[3-(meth)acryloxyethoxy-2-hydroxypropyloxypropyl]-terminated polydimethylsiloxane, α,ω-bis[3-(meth)acryloxyethylamino-2-hydroxypropyloxypropyl]-terminated polydimethylsiloxane, α,ω-bis[3-(meth)acrylamidoethoxy-2-hydroxypropyloxypropyl]-terminated polydimethylsiloxane, α,ω-bis[(meth)acrylamidoethylamino-2-hydroxypropyloxypropyl]-terminated polydimethylsiloxane, α,ω-bis[3-(meth)acryloxypropoxy-2-hydroxypropyloxypropyl]-terminated polydimethylsiloxane, α,ω-bis[3-(meth)acryloxypropylamino-2-hydroxypropyloxypropyl]-terminated polydimethylsiloxane, α,ω-bis[3-(meth)acrylamidopropoxy-2-hydroxypropyloxypropyl]-terminated polydimethylsiloxane, α,ω-bis[3-(meth)acrylamidopropylamino-2-hydroxypropyloxypropyl]-terminated polydimethylsiloxane, α,ω-bis[3-(meth)acrylamidoisopropoxy-2-hydroxypropyloxypropyl]-terminated polydimethylsiloxane, α,ω-bis(allyloxy-2-hydroxypropyl-oxyethoxypropyl)-terminated polydimethylsiloxane, α,ω-bis(allylamino-2-hydroxypropyloxypropyl)-terminated polydimethylsiloxane, α,ω-bis(vinylamino-2-hydroxypropyloxypropyl)-terminated polydimethylsiloxane, α,ω-bis(allyloxy-2-hydroxypropyl-oxypropyl)-terminated polydimethylsiloxane, α,ω-bis(vinyloxy-2-hydroxypropyl-oxyethoxypropyl)-terminated polydimethylsiloxane, α,ω-bis[(meth)acryloxy-2-hydroxypropyloxy-ethoxypropyl]-terminated polydimethylsiloxane, α,ω-bis[(meth)acryloxy-2-hydroxypropyl-N-ethylaminopropyl]-terminated polydimethylsiloxane, α,ω-bis[(meth)acryloxy-2-hydroxypropyl-aminopropyl]-polydimethylsiloxane, α,ω-bis[allyloxy-2-hydroxypropyl-N-ethylaminopropyl]-terminated polydimethylsiloxane, α,ω-bis[vinyloxy-2-hydroxypropyl-N-ethylaminopropyl]-terminated polydimethylsiloxane, α,ω-bis[(meth)acryloxy-2-hydroxypropyl-oxycabonylpropyl]-terminated polydimethylsiloxane, α,ω-bis[allyloxy-2-hydroxypropyl-oxycabonylpropyl]-terminated polydimethylsiloxane, α,ω-bis[vinyloxy-2-hydroxypropyl-oxycabonylpropyl]-terminated polydimethylsiloxane, α,ωbis[(meth)acryloxy-2-hydroxypropyl-oxy-pentylcabonyloxyalkyl]-terminated polydimethylsiloxane, α,ω-bis[allyloxy-2-hydroxypropyl-oxy-pentylcabonyloxyalkyl]-terminated polydimethylsiloxane, α,ω-bis[vinyloxy-2-hydroxypropyl-oxy-pentylcabonyloxyalkyl]-terminated polydimethylsiloxane, α,ω-bis(allyloxy-2-hydroxypropyl-oxy(polyethylenoxy)propyl)-terminated polydimethylsiloxane, α,ω-bis(vinyloxy-2-hydroxypropyl-oxy(polyethylenoxy)propyl)-terminated polydimethylsiloxane, α,ω-bis[(meth)acryloxy-2-hydroxypropyl-oxy(polyethylenoxy)propyl]-terminated polydimethylsiloxane, a coupling product of $C_2$-$C_4$ hydroxyalkyl(meth)acrylate or $C_2$-$C_4$ hydroxyalkyl(meth)acrylamide or (meth)acrylic acid with α,ω-bis(hydroxyethoxypropyl)-polydimethylsiloxane through a di-epoxy compound, or combinations thereof.

6. The chain-extended polysiloxane crosslinker of claim 5, wherein said at least one dimercaptan is selected from the group consisting of $C_2$-$C_{12}$ alkyl dimercaptans, ethylcyclohexyl dimercaptan, dipentene dimercaptan, benzenedithiol, methyl-substituted benzenedithiol, benzenedimethanethiol, glycol dimercaptoacetate, ethyl ether dimercaptan, triglycol dimercaptan, tetraglycol dimercaptan, and combinations thereof.

7. The chain-extended polysiloxane crosslinker of claim 5, wherein said at least one dimercaptan comprises at least one hydroxy and/or carboxyl group.

8. The chain-extended polysiloxane crosslinker of claim 3, wherein said at least one polysiloxane crosslinker is free of any hydroxy or carboxyl group, wherein said at least one dimercaptan comprises at least one hydroxy and/or carboxyl group.

9. The chain-extended polysiloxane crosslinker of claim 8, wherein said at least one dimercaptan is dimercaprol, dimercaptobutanol, dimercaptopentanol, dithiothreitol, dimercaptopropionic acid, dihydrolipoic acid, dimercaptosuccinic acid, or combinations thereof.

10. The chain-extended polysiloxane crosslinker of claim 8, wherein said at least one dimercaptan comprises at least one carboxyl group.

11. The chain-extended polysiloxane crosslinker of claim 10, wherein said at least one dimercaptan is dimercaptopropionic acid, dihydrolipoic acid, dimercaptosuccinic acid, or combinations thereof.

\* \* \* \* \*